United States Patent
Roux et al.

(10) Patent No.: US 9,969,715 B2
(45) Date of Patent: May 15, 2018

(54) COMPOUNDS USEFUL FOR TREATING CANCER

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Pierre Roux, Saint Gely du Fesc (FR); Florence Mahuteau, Saint Remy les Chevreuses (FR); Romain Najman, L'Hay les Roses (FR); Gilles Gadea, Matelles (FR); Jamal Tazi, Clapiers (FR); Didier Scherrer, Castelnau le Lez (FR); Carsten Brock, Montpellier (FR); Nathalie Cahuzac, Jacou (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days. days.

(21) Appl. No.: 14/432,328

(22) PCT Filed: Sep. 30, 2013

(86) PCT No.: PCT/IB2013/058992
§ 371 (c)(1),
(2) Date: Mar. 30, 2015

(87) PCT Pub. No.: WO2014/049578
PCT Pub. Date: Apr. 3, 2014

(65) Prior Publication Data
US 2015/0315173 A1    Nov. 5, 2015

(30) Foreign Application Priority Data
Sep. 28, 2012 (EP) .................................. 12186684

(51) Int. Cl.
C07D 213/75 (2006.01)
C07D 401/14 (2006.01)
C07D 401/12 (2006.01)
C07D 239/42 (2006.01)

(52) U.S. Cl.
CPC ......... *C07D 401/14* (2013.01); *C07D 213/75* (2013.01); *C07D 239/42* (2013.01); *C07D 401/12* (2013.01)

(58) Field of Classification Search
CPC .................................................. C07D 213/75
USPC .......................................... 546/309; 514/352
See application file for complete search history.

(56) References Cited

U.S. PATENT DOCUMENTS
2012/0053170 A1    3/2012    Arigon et al.

FOREIGN PATENT DOCUMENTS
WO    2009/087238 A2    7/2009
WO    2010/109122 A1    9/2010

OTHER PUBLICATIONS

Arcangeli et al., "Novel perspectives, etc.," Drug Resistance Updates 21-22 (2015) 11-19.*
Chambers et al., Dissemination and Growth of Cancer Cells in Metastatic Sites, Nature Reviews, vol. 2, pp. 663-672 (2002).*
Pearce et al., Failure modes in anticancer drug discovery and development, Cancer Drug Design and Discovery Edited by Stephen Neidle, Chapter 18, pp. 424-435 (2008).*
Bone Cancer, American Cancer Society, 42 pages (2014).*
Simone, Oncology:Introduction, Cecil Textbook of Medicine, ed Bennett et al. W.B.Saunders CO. 20th ed, vol. 1, 1996, pp. 1004-1010.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Golub et al., "Molecular Classification, etc.," Science, 286, 1999, 531-537.*
Wells et al., "The dormancy, etc.," Cancer Res., 2013, 3811-3816.*
Feb. 3, 2014 International Search Report issued in PCT/IB2013/058992.
Feb. 3, 2014 Written Opinion of the International Searching Authority issued in PCT/IB2013/058992.

* cited by examiner

*Primary Examiner* — Patricia L Morris
(74) *Attorney, Agent, or Firm* — Oliff PLC

(57) ABSTRACT

The present invention relates to a compound of formula (I):

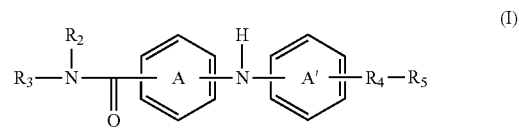

wherein A and A' independently represent a phenylene group or a pyridylene group; $R_2$ is a hydrogen atom or a $(C_1-C_4)$ alkyl group; $R_3$ is a 2-pyridyl group, 3-pyridyl group, a 4-pyridyl group, a 2-pyrimidinyl group, a 4-pyrimidinyl group or a 5-pyrimidinyl group; $R_4$ is a carbonyl group or a sulfonyl group; and $R_5$ is a —NH—$(CH_2)_a$—$NR_6R_7$ group or a 4-methylpiperazinyl group, with a being an integer from 1 to 4, $R_6$ and $R_7$ representing independently a $(C_1-C_4)$alkyl group, or $R_6$ and $R_7$ together with the nitrogen atom to which they are linked forming a heterocycle group which is chosen among a 4-methylpiperazinyl group, a morpholino group, a pyrrolidinyl group and a piperidino group; or any one of its pharmaceutically acceptable salt.

8 Claims, No Drawings

COMPOUNDS USEFUL FOR TREATING CANCER

The present invention is generally dedicated to the use of compounds for the manufacture of compositions useful to treat cancer.

In most of the cancers, mortality is not due to the primary tumor but rather to the derived metastases. This malignant progression which leads to tumor invasion and is clinically defined by the appearance of metastases is the final outcome of the primary loss of cell adhesion and increase of cell motility which together allow invasive cell to leave the initial tumor site and colonize various target tissues.

Metastases are considered as a recurrent feature of uncontrolled malignant progression of cancer. During this process, tumor cells complete their malignant transformation by increasing their migratory capacity. Cancer cells can then disseminate and establish tumor foci in far away sites. Spreading of cancer cells in the organism is the outcome of a series of events called <<metastatic cascade>>: invasion of the tissues around the tumor, venous or lymphatic intravasation, migration and establishment in a distant place of a new colony that escapes from all the defence mechanisms of the organism.

Metastatic invasion, against which there is no efficient therapeutic option available at this time, is by far the major cause of death. Due to the frequency of cancers diagnosed at the metastatic stage and to the therapeutic impasse they represent, the development of molecules that specifically target metastatic invasion is thus a crucial requirement for a major breakthrough in cancer treatments.

Document WO2009/087238 describes compounds which may be useful to treat cancer. As it comes out from example 17 herein after, comparative data are provided wherein a close compound as disclosed in said document is surprisingly less active in invasion test than a claimed compound.

It has now been found that derivatives of formula (I) as defined hereinafter are able to prevent, as illustrated in the experimental data hereinafter, the invasive progression of metastatic cancers, and on the basis of such activity, the compounds are useful in the treatment of cancer.

The present invention therefore relates to compounds of formula (I) and their pharmaceutically acceptable salts, as such, as defined below.

Further, the present invention relates to compounds of formula (I) as defined below for use as medicines and more particularly for use for preventing and/or inhibiting and/or treating cancer.

The present invention moreover relates to a method of preventing, inhibiting or treating cancer, which comprises at least one step consisting in administering to a patient suffering therefrom an effective amount of a compound as defined in formula (I) below or one of its pharmaceutically acceptable salts.

The present invention further relates to a process for the preparation of said compounds of formula (I).

The present invention also provides pharmaceutical compositions comprising at least one of said compounds of formula (I).

According to one aspect, a subject-matter of the present invention relates to a compound of formula (I)

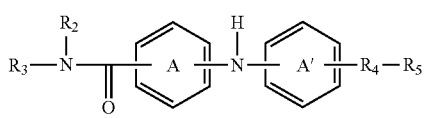

(I)

wherein
A and A' independently represent a phenylene group or a pyridylene group;
$R_2$ is a hydrogen atom or a $(C_1$-$C_4)$alkyl group;
$R_3$ is a 2-pyridyl group, 3-pyridyl group, a 4-pyridyl group, a 2-pyrimidinyl group, a 4-pyrimidinyl group or a 5-pyrimidinyl group;
$R_4$ is a carbonyl group or a sulfonyl group; and
$R_5$ is a —NH—$(CH_2)_a$—$NR_6R_7$ group or a 4-methylpiperazinyl group, with a being an integer from 1 to 4, $R_6$ and $R_7$ representing independently a $(C_1$-$C_4)$alkyl group, or $R_6$ and $R_7$ together with the nitrogen atom to which they are linked forming a heterocycle group which is chosen among a 4-methylpiperazinyl group, a morpholino group, a pyrrolidinyl group and a piperidino group;
or any one of its pharmaceutically acceptable salt.

According to a preferred embodiment, the present invention relates to a compound of formula (I) wherein the group —NH— between A and A' and the group —R4-R5 are in position meta from each other with respect to A'.

According to a preferred embodiment, the present invention relates to a compound of formula (A1)

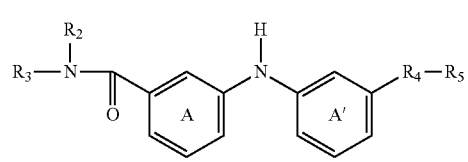

(A1)

wherein A, A', $R_2$, $R_3$, $R_4$ and $R_5$ are as defined above.

The present invention encompasses the embodiments which are described hereinafter wherein the positions of the substitution groups on A and A' are in conformity with the structure of formula (A1) as described above, i.e. meta position on A and meta position on A'.

According to another preferred aspect, the present invention relates to a compound of formula (I) as defined above, wherein
A and A' independently represent a phenylene group or a pyridylene group;
$R_2$ is a hydrogen atom or a methyl group;
$R_3$ is a 2-pyridyl group, a 4-pyridyl group or a 4-pyrimidinyl group;
$R_4$ is a carbonyl group or a sulfonyl group; and
$R_5$ is a —NH—$(CH_2)_a$—$NR_6R_7$ group or a 4-methylpiperazinyl group, with a being an integer from 2 to 3, $R_6$ and $R_7$ representing an ethyl group, or $R_6$ and $R_7$ together with the nitrogen atom to which they are linked forming a heterocycle group which is chosen among a 4-methylpiperazinyl group, a morpholino group, a pyrrolidinyl group and a piperidino group;
or any one of its pharmaceutically acceptable salt.

According to a more preferred aspect, the present invention relates to a compound of formula (I')

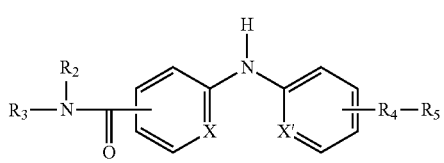

wherein
X and X' are independently CH or N;
$R_2$ is a hydrogen atom or a methyl group;

R$_3$ is a 2-pyridyl group, a 4-pyridyl group or a 4-pyrimidinyl group;

R$_4$ is a carbonyl group or a sulfonyl group; and

R$_5$ is a —NH—(CH$_2$)$_a$—NR$_6$R$_7$ group or a 4-methylpiperazinyl group, with a being an integer from 2 to 3, R$_6$ and R$_7$ representing an ethyl group, or R$_6$ and R$_7$ together with the nitrogen atom to which they are linked forming a heterocycle group which is chosen among a 4-methylpiperazinyl group, a morpholino group, a pyrrolidinyl group and a piperidino group;

or any one of its pharmaceutically acceptable salt.

According to a particular embodiment, an additional subject-matter of the present invention is a compound of formula (Ia)

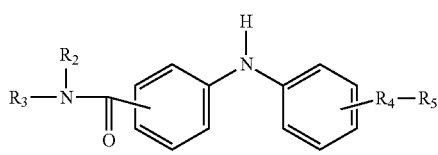

(Ia)

wherein R$_2$, R$_3$, R$_4$ and R$_5$ are as defined above;
or any one of its pharmaceutically acceptable salt.

According to a preferred embodiment, the present invention relates to a compound of formula (Ia) wherein the group —R4-R5 is in meta position with respect to the group —NH— between the two phenyl groups.

According to a more preferred embodiment, the present invention relates to a compound of formula (Ia) as defined above, wherein R$_4$ is a carbonyl group and R$_2$, R$_3$ and R$_5$ are as defined above, or any one of its pharmaceutically acceptable salt.

Also disclosed is a compound of formula (Ib)

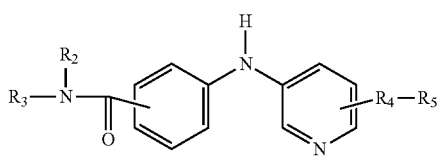

(Ib)

wherein R$_2$, R$_3$, R$_4$ and R$_5$ are as defined above;
or any one of its pharmaceutically acceptable salt.

According to a preferred embodiment, the present invention relates to a compound of formula (Ib) wherein the group —R4-R5 is in meta position with respect to the group —NH— between the phenyl group and the pyridine group.

More preferably, in formula (Ib), R2 is a hydrogen atom; R3 is a 4-pyridyl group; R4 is a carbonyl group; and R5 is a —NH—(CH2)a-NR6R7 group, with a being an integer 3, and R6 and R7 representing an ethyl group; or any one of its pharmaceutically acceptable salt.

According to another particular embodiment, an additional subject-matter of the present invention is a compound of formula (Ic)

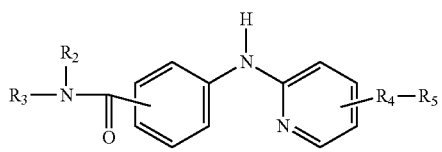

(Ic)

wherein R$_2$, R$_3$, R$_4$ and R$_5$ are as defined above;
or any one of its pharmaceutically acceptable salt.

According to a preferred embodiment, the present invention relates to a compound of formula (Ic) wherein the group —R4-R5 is in meta position with respect to the group —NH— between the phenyl group and the pyridine group.

According to a more preferred embodiment, the present invention relates to a compound of formula (Ic) as defined above wherein R$_2$ is a hydrogen atom or a methyl group; R$_3$ is a 4-pyridyl group or a 4-pyrimidinyl group; R$_4$ is a carbonyl group; and R$_5$ is a —NH—(CH$_2$)$_a$—NR$_6$R$_7$ group, a being an integer 3, R$_6$ and R$_7$ representing an ethyl group, or R$_6$ and R$_7$ together with the nitrogen atom to which they are linked forming a heterocycle group which is a 4-methylpiperazinyl group; or any one of its pharmaceutically acceptable salt.

According to another particular embodiment, an additional subject-matter of the present invention is a compound of formula (Id)

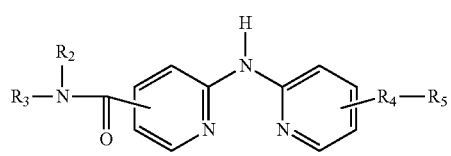

(Id)

wherein R$_2$, R$_3$, R$_4$ and R$_5$ are as defined above;
or any one of its pharmaceutically acceptable salt.

According to a preferred embodiment, the present invention relates to a compound of formula (Id) wherein the group —R4-R5 is in meta position with respect to the group —NH— between the two pyridine groups.

According to a more preferred embodiment, the present invention relates to a compound of formula (Id) as defined above, wherein R$_2$ is a hydrogen atom; R$_3$ is a 4-pyridyl group; R$_4$ is a carbonyl group; and R$_5$ is a —NH—(CH$_2$)$_a$—NR$_6$R$_7$ group, a being an integer 3, R$_6$ and R$_7$ representing an ethyl group, or R$_6$ and R$_7$ together with the nitrogen atom to which they are linked forming a heterocycle group which is a 4-methylpiperazinyl group; or any one of its pharmaceutically acceptable salt.

According to another particular embodiment, an additional subject-matter of the present invention is a compound of formula (Ie)

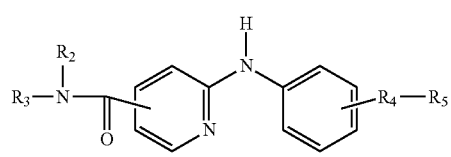

(Ie)

wherein R$_2$, R$_3$, R$_4$ and R$_5$ are as defined above;
or any one of its pharmaceutically acceptable salt.

According to a preferred embodiment, the present invention relates to a compound of formula (Ib) wherein the group —R4-R5 is in meta position with respect to the group —NH— between the phenyl group and the pyridine group.

According to a more preferred embodiment, the present invention relates to a compound of formula (Ie) as defined above, wherein R$_2$ is a hydrogen atom; R$_3$ is a 4-pyridyl group; R$_4$ is a carbonyl group or a sulfonyl group; and R$_5$ is a —NH—(CH$_2$)$_a$—NR$_6$R$_7$ group, a being an integer 3, R$_6$ and R$_7$ representing an ethyl group, or R$_6$ and R$_7$ together with the nitrogen atom to which they are linked forming a heterocycle group which is chosen among a 4-methylpiperazinyl group, a morpholino group, a pyrrolidinyl group and a piperidino group; or any one of its pharmaceutically acceptable salt.

According to a preferred embodiment of the present invention, a compound of formula (I) is chosen among:

(1) N-(3-(diethylamino)propyl)-3-((3-(pyridin-4-ylcarbamoyl)phenyl)amino)benzamide
(2) 3-((4-((3-(diethylamino)propyl)carbamoyl)phenyl)amino)-N-(pyridin-4-yl)benzamide
(3) N-(3-morpholinopropyl)-3-((3-(pyridin-4-ylcarbamoyl)phenyl)amino)benzamide
(4) N-(pyridin-4-yl)-3-((3-((3-(pyrrolidin-1-yl)propyl)carbamoyl)phenyl)amino)benzamide
(5) 3-((3-(N-(3-(diethylamino)propyl)sulfamoyl)phenyl)amino)-N-(pyridin-4-yl)benzamide
(6) N-(3-(4-methylpiperazin-1-yl)propyl)-3-((3-(pyridin-4-ylcarbamoyl)phenyl)amino)benzamide
(7) N-(3-(piperidin-1-yl)propyl)-3-((3-(pyridin-4-ylcarbamoyl)phenyl)amino)benzamide
(8) 3-((3-(4-methylpiperazine-1-carbonyl)phenyl)amino)-N-(pyridin-4-yl)benzamide
(9) 3-((3-(N-(3-(piperidin-1-yl)propyl)sulfamoyl)phenyl)amino)-N-(pyridin-4-yl)benzamide
(10) 3-((3-(N-(2-(piperidin-1-yl)ethyl)sulfamoyl)phenyl)amino)-N-(pyridin-4-yl)benzamide
(11) N-(3-(diethylamino)propyl)-3-((3-(pyridin-2-ylcarbamoyl)phenyl)amino)benzamide
(12) 3-((3-(N-(3-morpholinopropyl)sulfamoyl)phenyl)amino)-N-(pyridin-4-yl)benzamide
(13) N-(3-(diethylamino)propyl)-3-((4-(pyridin-4-ylcarbamoyl)phenyl)amino)benzamide
(14) N-(3-morpholinopropyl)-3-((4-(pyridin-4-ylcarbamoyl)phenyl)amino)benzamide
(15) 4-((3-(N-(3-morpholinopropyl)sulfamoyl)phenyl)amino)-N-(pyridin-4-yl)benzamide
(16) N-(pyridin-4-yl)-4-((3-(N-(2-(pyrrolidin-1-yl)ethyl)sulfamoyl)phenyl)amino)benzamide
(17) 3-((3-((3-(diethylamino)propyl)carbamoyl)phenyl)amino)-N-methyl-N-(pyridin-4-yl)benzamide
(18) N-methyl-N-(pyridin-4-yl)-3-((3-((3-(pyrrolidin-1-yl)propyl)carbamoyl)phenyl)amino)benzamide
(19) 3-((3-(N-(3-(diethylamino)propyl)sulfamoyl)phenyl)amino)-N-methyl-N-(pyridin-4-yl)benzamide
(20) N-methyl-3-((3-((3-(4-methylpiperazin-1-yl)propyl)carbamoyl)phenyl)amino)-N-(pyridin-4-yl)benzamide
(21) N-methyl-3-((3-((3-(piperidin-1-yl)propyl)carbamoyl)phenyl)amino)-N-(pyridin-4-yl)benzamide
(22) N-methyl-3-((3-((3-morpholinopropyl)carbamoyl)phenyl)amino)-N-(pyridin-4-yl)benzamide
(23) N-methyl-3-((3-(N-(3-morpholinopropyl)sulfamoyl)phenyl)amino)-N-(pyridin-4-yl)benzamide
(24) N-methyl-3-((3-(N-(3-(piperidin-1-yl)propyl)sulfamoyl)phenyl)amino)-N-(pyridin-4-yl)benzamide
(25) N-(3-(diethylamino)propyl)-3-((3-(pyrimidin-4-ylcarbamoyl)phenyl)amino)benzamide
(26) 3-((3-(N-(3-(diethylamino)propyl)sulfamoyl)phenyl)amino)-N-(pyrimidin-4-yl)benzamide
(27) 3-((3-(N-(3-(piperidin-1-yl)propyl)sulfamoyl)phenyl)amino)-N-(pyrimidin-4-yl)benzamide
(28) N-(pyrimidin-4-yl)-3-((3-((3-(pyrrolidin-1-yl)propyl)carbamoyl)phenyl)amino)benzamide
(29) N-(3-(piperidin-1-yl)propyl)-3-((3-(pyrimidin-4-ylcarbamoyl)phenyl)amino)benzamide
(30) N-(3-morpholinopropyl)-3-((3-(pyrimidin-4-ylcarbamoyl)phenyl)amino)benzamide
(31) N-(3-(4-methylpiperazin-1-yl)propyl)-3-((3-(pyrimidin-4-ylcarbamoyl)phenyl)amino)benzamide
(32) N-(3-(diethylamino)propyl)-5-((3-(pyridin-4-ylcarbamoyl)phenyl)amino) nicotinamide
(33) N-(3-(diethylamino)propyl)-2-((3-(pyridin-4-ylcarbamoyl)phenyl)amino) isonicotinamide
(34) N-(3-(4-methylpiperazin-1-yl)propyl)-2-((3-(pyridin-4-yl)carbamoyl)-phenyl)amino) isonicotinamide
(35) N-(3-(diethylamino)propyl)-6-((3-(pyridin-4-ylcarbamoyl)phenyl)amino)picolinamide
(36) N-(3-(diethylamino)propyl)-6-((4-(pyridin-4-ylcarbamoyl)phenyl)amino)picolinamide
(37) N-(3-(diethylamino)propyl)-6-((3-(methyl(pyridin-4-yl)carbamoyl)phenyl)amino)picolinamide
(38) N-(3-(diethylamino)propyl)-2-((3-(methyl(pyridin-4-yl)carbamoyl)phenyl)amino)isonicotinamide
(39) 2-((3-(methyl(pyridin-4-yl)carbamoyl)phenyl)amino)-N-(3-(4-methylpiperazin-1-yl)propyl)isonicotinamide
(40) N-(3-(diethylamino)propyl)-6-((3-(pyrimidin-4-ylcarbamoyl)phenyl)amino)picolinamide
(41) N-(3-(diethylamino)propyl)-2-((3-(pyrimidin-4-ylcarbamoyl)phenyl)amino)isonicotinamide
(42) N-(3-(4-methylpiperazin-1-yl)propyl)-2-((3-(pyrimidin-4-ylcarbamoyl)phenyl)amino)isonicotinamide
(43) N-(3-(diethylamino)propyl)-6-((4-(pyridin-4-ylcarbamoyl)pyridin-2-yl)amino)picolinamide
(44) N-(3-(diethylamino)propyl)-2-((4-(pyridin-4-ylcarbamoyl)pyridin-2-yl)amino)isonicotinamide
(45) N-(3-(4-methylpiperazin-1-yl)propyl)-2-((4-(pyridin-4-ylcarbamoyl)pyridin-2-yl)amino)isonicotinamide
(46) 2-((3-(N-(3-(diethylamino)propyl)sulfamoyl)phenyl)amino)-N-(pyridin-4-yl)isonicotinamide
(47) 2-(3-((3-(diethylamino)propyl)carbamoyl)phenyl)amino)-N-(pyridin-4-yl)isonicotinamide
(48) 2-((3-((3-morpholinopropyl)carbamoyl)phenyl)amino)-N-(pyridin-4-yl) isonicotinamide
(49) N-(3-(piperidin-1-yl)propyl)-3-((3-(pyridin-4-ylcarbamoyl)phenyl)amino)benzamide
(50) N-(pyridin-4-yl)-2-((3-((3-(pyrrolidin-1-yl)propyl)carbamoyl)phenyl)amino) isonicotinamide
(51) 2-((3-((3-(4-methylpiperazin-1-yl)propyl)carbamoyl)phenyl)amino)-N-(pyridin-4-yl)isonicotinamide The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I), (I'), (Ia), (Ib), (Ic), (Id) and (Ie) and or salts thereof may form solvates (e.g. hydrates) and the invention includes all such solvates.

Therefore, the present invention extends to compounds (1) to (51), their pharmaceutically acceptable salts, their solvates and hydrates thereof, as such.

In the context of the present invention, the term:
"($C_1$-$C_4$)alkyl" as used herein respectively refers to $C_1$-$C_4$ normal, secondary or tertiary saturated hydrocarbon. Examples are, but are not limited to, methyl, ethyl, 1-propyl, 2-propyl, butyl, isobutyl, tert-butyl, and
"patient" may extend to humans or mammals, such as cats or dogs.

A compound of formulae (I), (I'), (Ia), (Ib), (Ic), (Id) and (Ie) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

According to another aspect, the present invention relates to a compound of formulae (I), (I'), (Ia), (Ib), (Ic), (Id) and (Ie) for use as a medicine.

According to another aspect, the present invention relates to a compound of formulae (I), (I'), (Ia), (Ib), (Ic), (Id) and (Ie) for use for preventing and/or inhibiting and/or treating cancer.

According to the present invention, the term "preventing" or "prevention" means to reduce the risk of onset or slow the occurrence of a given phenomenon, namely, a cancer.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

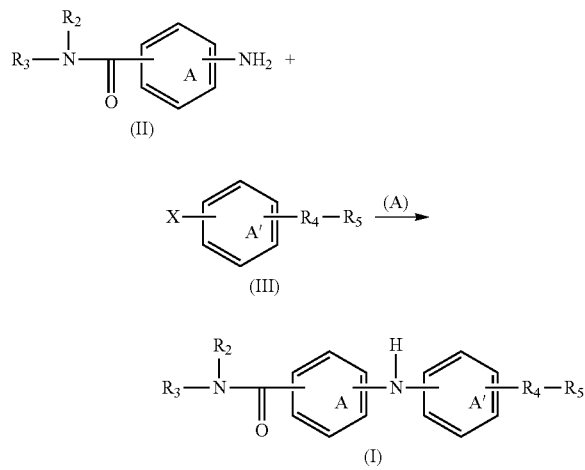

The synthesis is based on a coupling reaction starting from a halogeno aromatic compound of formula (III), wherein $R_4$ and $R_5$ are as defined above and X is a chlorine atom, an iodine atom or a bromine atom.

According to route (A), the compound of formula (III) is placed in a protic solvent such as tert-butanol. The compound of formula (II) in which $R_2$, $R_3$ and A are as defined above, is then added in a molar ratio ranging from 1 to 1.5 with respect to the compound of formula (III) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of an organometallic catalyst, such as $Pd(OAc)_2$ or $Pd_2dba_3$ in an amount ranging from 2 mol % to 10 mol % relative to the total amount of compound of formula (III). The reaction mixture can then be heated at a temperature ranging from 80 to 120° C., for example at 90° C. and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give product (I).

The starting compounds of formula (II) and (III) are available or can be prepared according to methods known to the person skilled in the art.

More particularly, compounds of formula (II) (i.e. respectively (IIa) and (IIc)) when used to prepare compounds of formulae (Ia) and (Ic) can be prepared according to scheme 2 below.

Preparation of intermediate compounds of formula (II) for compounds of formulae (Ia) and (Ic), with one of $X_1$ or $X_2$ being N, and the other of $X_1$ and $X_2$ being CH ($R_3$ is a pyridyl group).

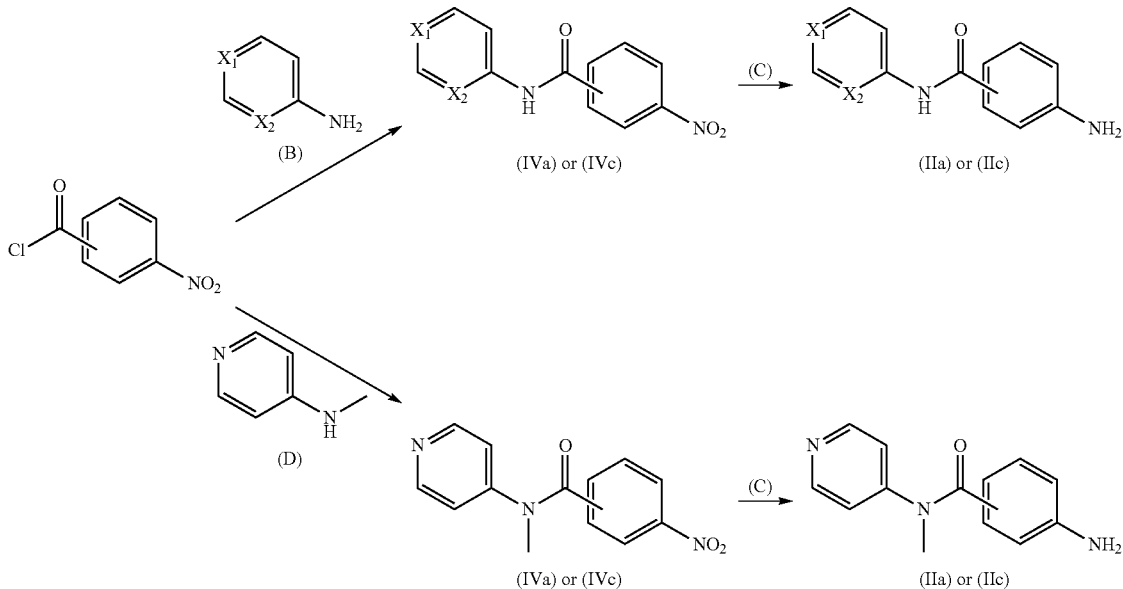

As shown in scheme 2, intermediate compounds of formulae (IIa) and (IVa) are useful for preparing compounds of formula (Ia) according to the invention and intermediate compounds of formulae (IIc) and (IVc) are useful for preparing compounds of formula (Ic) according to the invention.

According to route (B), the aminopyridine, added in a molar ratio ranging from 1 to 1.5 with respect to the nitrobenzoyl chloride, is placed in an aqueous solution of inorganic base such as sodium hydroxide in a molar concentration ranging from 2M to 5M. A polar aprotic solvent such as dichloromethane is added to the solution, the reaction mixture can be cooled down to 0° C. with an ice bath and a solution of the nitrobenzoyl chloride in a polar aprotic solvent such as dichloromethane can be added dropwise. The reaction mixture can then be stirred at room temperature for a time ranging from 15 to 24 hours, for example 18 hours, under inert gas for example argon. The resulting precipitate can be filtered, washed with water and dichloromethane and dried under vacuum overnight to give product (IVa) or (IVc).

According to route (C), the compound of formula (IVa) or (IVc) and 10% Pd/C in a ratio ranging from 2% to 10% relative to the amount of benzamide are placed in a protic solvent such as ethanol. The reaction mixture can then be stirred at room temperature for a time ranging from 5 to 20 hours for example 16 hours under an atmosphere of $H_2$. The reaction mixture can then be filtered and the filtrate can be concentrated under reduced pressure to give product (IIa) or (IIc).

According to route (D), 4-(methylamino)pyridine is placed in a polar aprotic solvent such as dichloromethane. The nitrobenzoyl chloride is then added in a molar ratio ranging from 1 to 1.5 with respect to 4-(methylamino)pyridine, in presence of an organic base such as N,N-diisopropylethylamine or triethylamine in a molar ratio ranging from 1 to 2, in the presence of a nucleophilic catalyst such as dimethylaminopyridine in a molar ratio ranging from 0.1 to 1. The reaction mixture can then be stirred at room temperature for a time ranging from 5 to 20 hours for example 18 hours, under inert gas and for example argon. The organic phase can be washed with water, decanted and dried over magnesium sulphate. Finally, solid can be dried under vacuum overnight to give product (IVa) or (IVc).

More particularly, compounds of formula (II), when used to prepare compounds of formula (Ia) and (Ic) in one case or (Id) and (Ie) in another case, can be prepared according to scheme 3 below.

Preparation of intermediate compounds of formula (II) for compounds of formulae (Ia) and (Ic), with $X_1$ being CH and $X_2$ being N ($R_3$ is a pyrimidinyl group), and for compounds of formulae (Id) and (Ie), with $X_1$ being N and $X_2$ being CH ($R_3$ is a pyridyl group).

Scheme 3

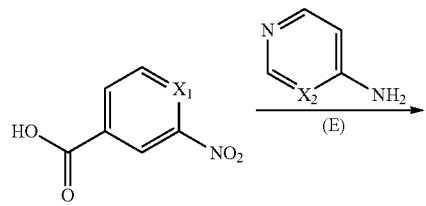

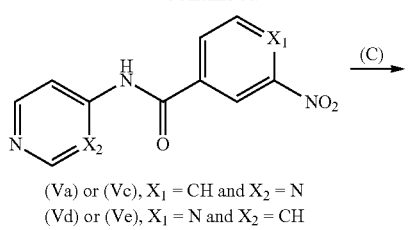

(Va) or (Vc), $X_1$ = CH and $X_2$ = N
(Vd) or (Ve), $X_1$ = N and $X_2$ = CH

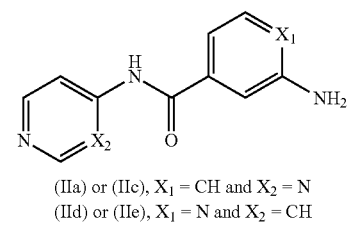

(IIa) or (IIc), $X_1$ = CH and $X_2$ = N
(IId) or (IIe), $X_1$ = N and $X_2$ = CH As shown in scheme 3, intermediate compounds of formulae (IIa) and (Va) are useful for preparing compounds of formula (Ia) according to the invention, intermediate compounds of formulae (IIc) and (Vc) are useful for preparing compounds of formula (Ic) according to the invention, intermediate compounds of formulae (IId) and (Vd) are useful for preparing compounds of formula (Id) according to the invention, and intermediate compounds of formulae (IIe) and (Ve) are useful for preparing compounds of formula (Ie) according to the invention.

According to route (E), the carboxylic acid derivative is placed in a polar aprotic solvent such as dichloromethane. The amino derivative is then added in a molar ratio ranging from 1 to 1.5 with respect to the carboxylic acid moiety, in presence of a coupling agent such as EDCI.HCl in a molar ratio ranging from 1 to 3, in presence of an organic base such as N,N-diisopropylethylamine or triethylamine in a molar ratio ranging from 1 to 3 and in the presence of a nucleophilic catalyst such as dimethylaminopyridine in a molar ratio ranging from 0.1 to 1. The reaction mixture can then be stirred at room temperature for a time ranging from 5 to 20 hours for example 18 hours, under inert gas and for example argon. The resulting precipitate can be filtered and washed with water and dichloromethane. The organic filtrate can be washed with water, decanted and dried over magnesium sulphate. Finally, solids can be gathered and dried under vacuum overnight to give product (Va), (Vc), (Vd) or (Ve).

Similarly, in order to obtain compounds of formula (Ib), either scheme 2 or scheme 3 can be used.

The chemical structures and spectroscopic data of some compounds of formula (I) of the invention are illustrated respectively in the following Table I and Table II.

TABLE I

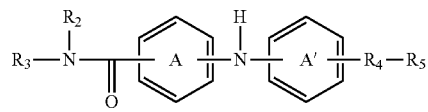

Formula (Ia)

1. [Structure: 4-pyridyl-NH-C(O)-phenyl(1,3)-NH-phenyl(1,3)-C(O)-NH-(CH2)3-N(Et)2]

2. [Structure: 4-pyridyl-NH-C(O)-phenyl(1,3)-NH-phenyl(1,4)-C(O)-NH-(CH2)3-N(Et)2]

3. [Structure: 4-pyridyl-NH-C(O)-phenyl(1,3)-NH-phenyl(1,3)-C(O)-NH-(CH2)3-morpholine]

4. [Structure: 4-pyridyl-NH-C(O)-phenyl(1,3)-NH-phenyl(1,3)-C(O)-NH-(CH2)3-pyrrolidine]

5. [Structure: 4-pyridyl-NH-C(O)-phenyl(1,3)-NH-phenyl(1,3)-S(O)2-NH-(CH2)3-N(Et)2]

6. [Structure: 4-pyridyl-NH-C(O)-phenyl(1,3)-NH-phenyl(1,3)-C(O)-NH-(CH2)3-N-methylpiperazine]

7. [Structure: 4-pyridyl-NH-C(O)-phenyl(1,3)-NH-phenyl(1,3)-C(O)-NH-(CH2)3-piperidine]

8. [Structure: 4-pyridyl-NH-C(O)-phenyl(1,3)-NH-phenyl(1,3)-C(O)-N(4-methylpiperazine)]

TABLE I-continued
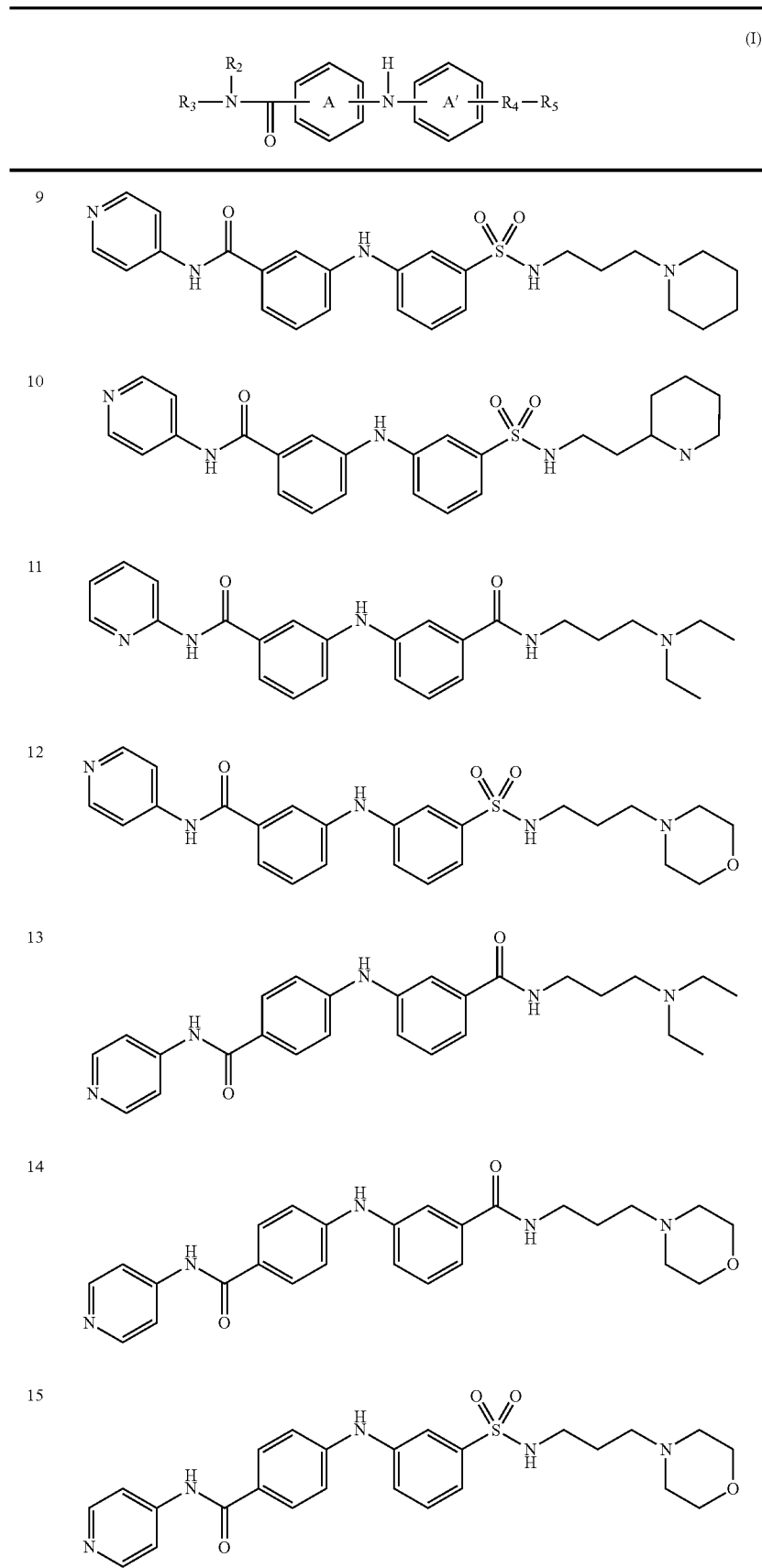

TABLE I-continued
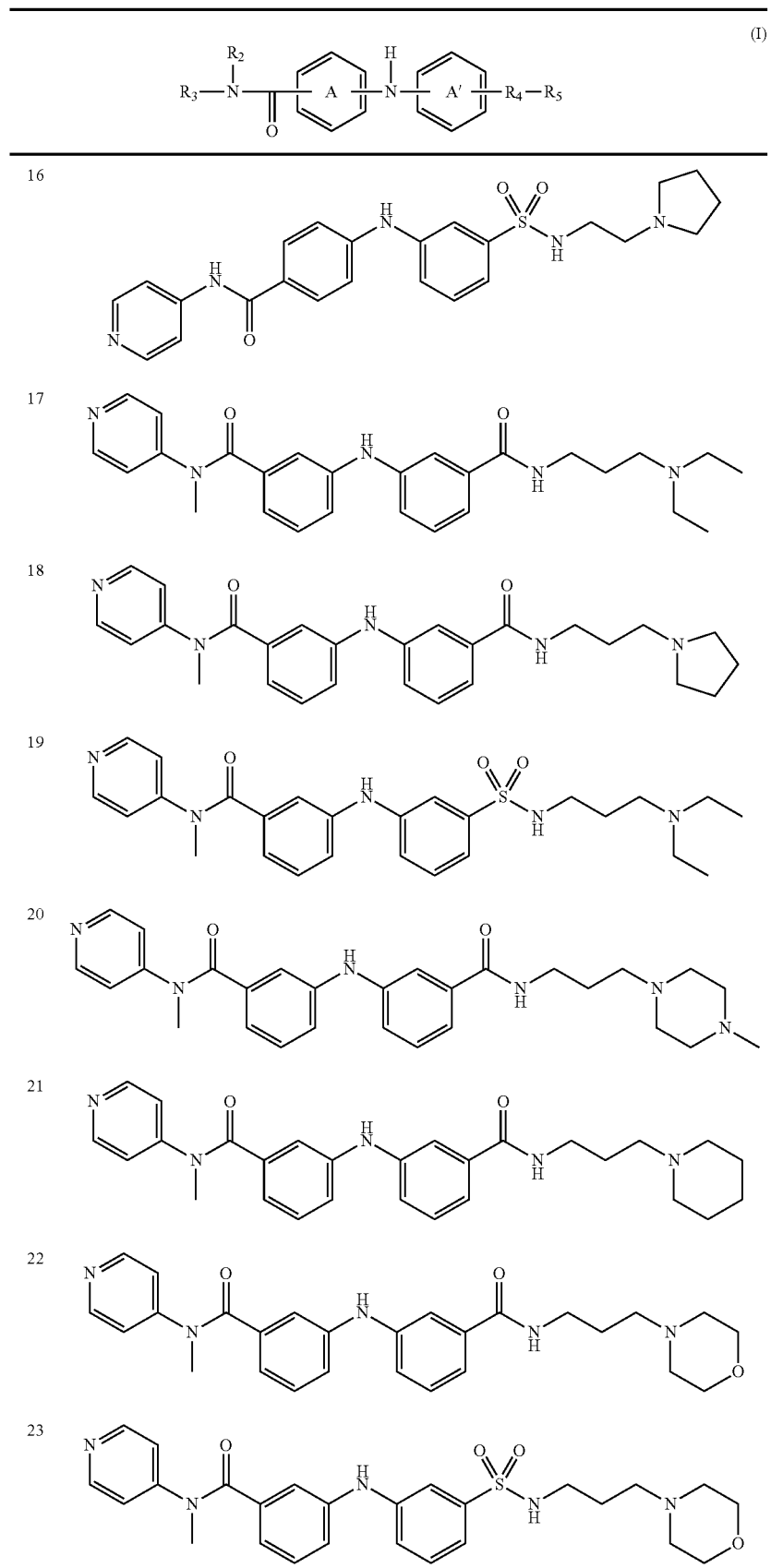

TABLE I-continued

| | Structure |
|---|---|
| 24 | N-(3-((3-(N-methyl-N-(pyridin-4-yl))carbamoyl)phenyl)amino)phenyl)-3-(piperidin-1-yl)propane-1-sulfonamide |
| 25 | 3-((3-((diethylamino)propyl)carbamoyl)phenyl)amino)-N-(pyrimidin-4-yl)benzamide |
| 26 | N-(3-(diethylamino)propyl)-3-((3-((pyrimidin-4-yl)carbamoyl)phenyl)amino)benzenesulfonamide |
| 27 | 3-(piperidin-1-yl)-N-(3-((3-((pyrimidin-4-yl)carbamoyl)phenyl)amino)phenyl)propane-1-sulfonamide |
| 28 | 3-((3-((3-(pyrrolidin-1-yl)propyl)carbamoyl)phenyl)amino)-N-(pyrimidin-4-yl)benzamide |
| 29 | 3-((3-((3-(piperidin-1-yl)propyl)carbamoyl)phenyl)amino)-N-(pyrimidin-4-yl)benzamide |
| 30 | 3-((3-((3-morpholinopropyl)carbamoyl)phenyl)amino)-N-(pyrimidin-4-yl)benzamide |

TABLE I-continued
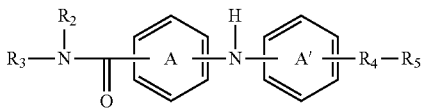
| 31 | 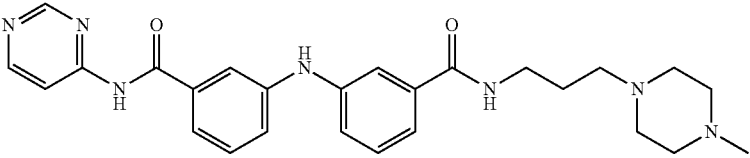 [SMILES: CN1CCN(CCCNC(=O)c2cccc(Nc3cccc(C(=O)Nc4ccncn4)c3)c2)CC1] |
| --- | --- |
| | Formula (Ib) |
| 32 | 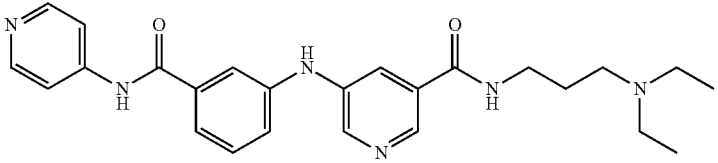 [SMILES: CCN(CC)CCCNC(=O)c1cncc(Nc2cccc(C(=O)Nc3ccncc3)c2)c1] |
| | Formula (Ic) |
| 33 | 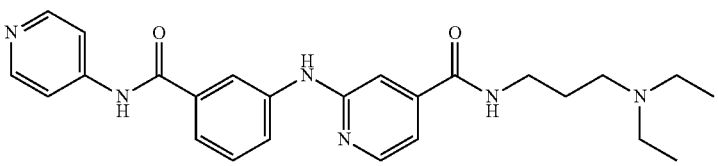 [SMILES: CCN(CC)CCCNC(=O)c1ccnc(Nc2cccc(C(=O)Nc3ccncc3)c2)c1] |
| 34 | 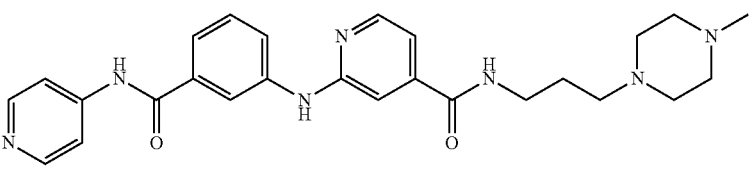 [SMILES: CN1CCN(CCCNC(=O)c2ccnc(Nc3cccc(C(=O)Nc4ccncc4)c3)c2)CC1] |
| 35 | 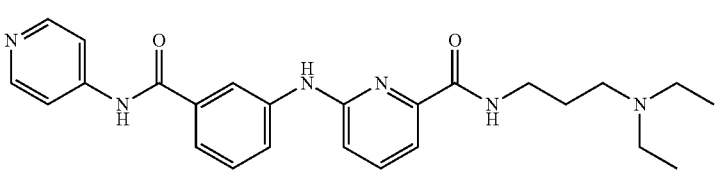 [SMILES: CCN(CC)CCCNC(=O)c1cccc(Nc2cccc(C(=O)Nc3ccncc3)c2)n1] |
| 36 | 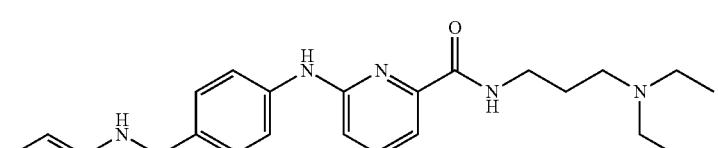 |

TABLE I-continued
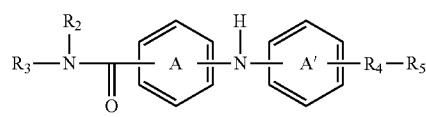
(I)
| 37 | 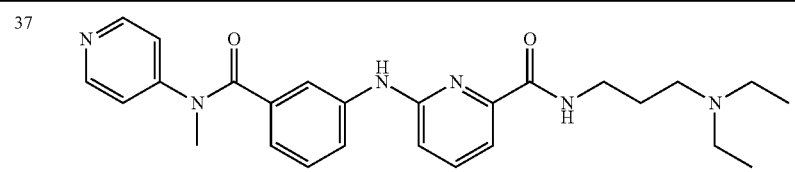 |
| --- | --- |
| 38 | 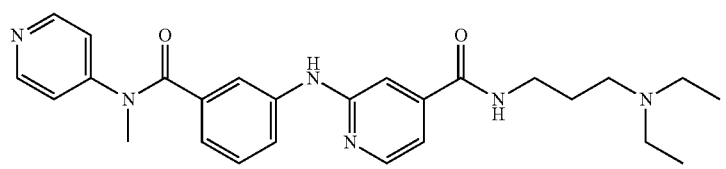 [SMILES: CCN(CC)CCCNC(=O)c1ccnc(Nc2cccc(C(=O)N(C)c3ccncc3)c2)c1] |
| 39 | 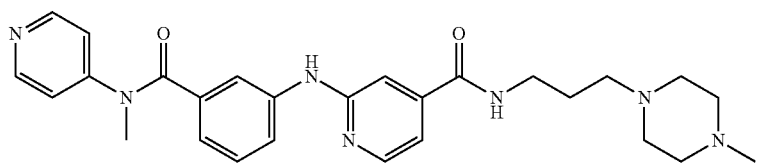 [SMILES: CN1CCN(CCCNC(=O)c2ccnc(Nc3cccc(C(=O)N(C)c4ccncc4)c3)c2)CC1] |
| 40 | 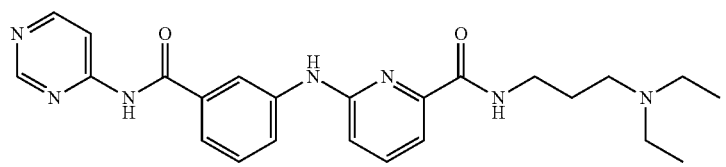 [SMILES: CCN(CC)CCCNC(=O)c1cccc(Nc2cccc(C(=O)Nc3ccncn3)c2)n1] |
| 41 | 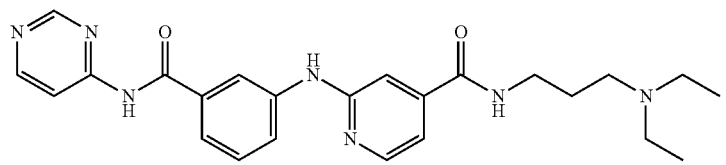 [SMILES: CCN(CC)CCCNC(=O)c1ccnc(Nc2cccc(C(=O)Nc3ccncn3)c2)c1] |
| 42 | 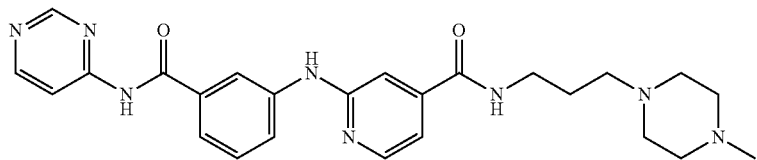 [SMILES: CN1CCN(CCCNC(=O)c2ccnc(Nc3cccc(C(=O)Nc4ccncn4)c3)c2)CC1] |
Formula (Id)
| 43 | 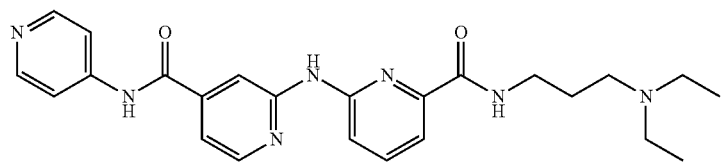 [SMILES: CCN(CC)CCCNC(=O)c1cccc(Nc2cc(C(=O)Nc3ccncc3)ccn2)n1] |
| --- | --- |
| 44 | 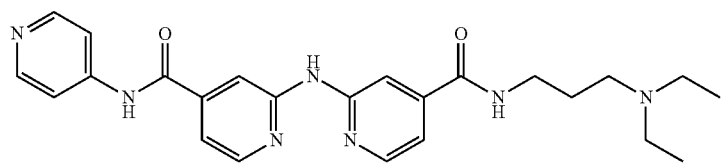 [SMILES: CCN(CC)CCCNC(=O)c1ccnc(Nc2cc(C(=O)Nc3ccncc3)ccn2)c1] |

TABLE I-continued
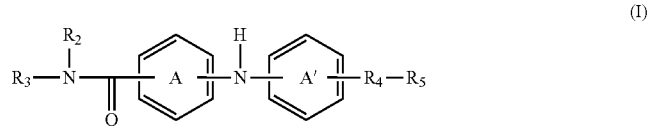
(I)
| 45 | 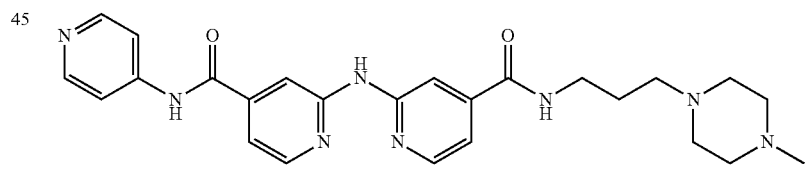 |
|---|---|
| | Formula (Ie) |
| 46 | 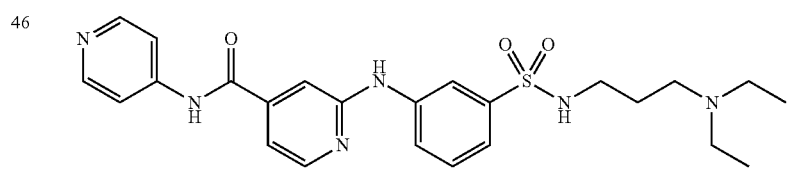 |
| 47 | 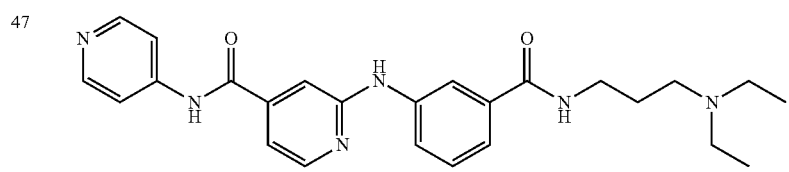 |
| 48 | 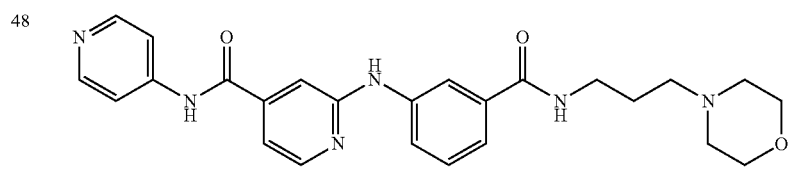 |
| 49 | 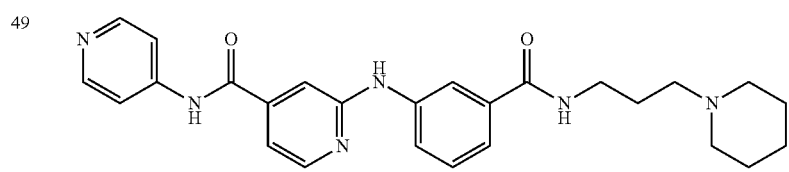 |
| 50 | 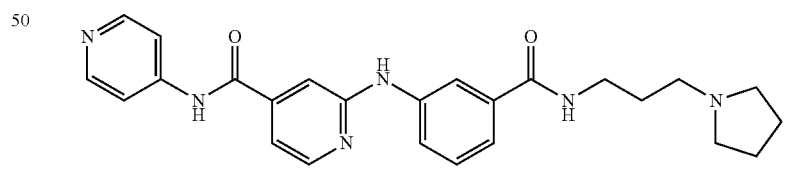 |
| 51 | 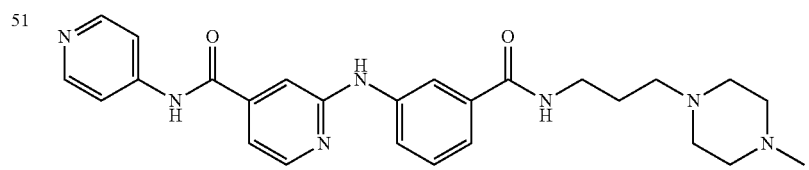 |

TABLE II

| Ex | Characterizations |
|---|---|
| 1 | $^1$H NMR (300 MHz, MeOD) δ 8.43 (dd, J = 4.9, 1.6 Hz, 2H), 7.83 (dd, J = 4.9, 1.6 Hz, 2H), 7.65 (t, J = 1.5 Hz, 1H), 7.58 (t, J = 1.7 Hz, 1H), 7.43 (t, J = 1.8 Hz, 1H), 7.40 (s, 1H), 7.35 (d, J = 2.1 Hz, 1H), 7.33 (t, J = 2.5 Hz, 1H), 7.31-7.28 (m, 2H), 3.39 (t, J = 6.8 Hz, 2H), 2.65-2.51 (m, 6H), 1.79 (q, J = 7.1 Hz, 2H), 1.04 (t, J = 7.2 Hz, 6H)<br>$^{13}$C NMR (75 MHz, MeOD) δ 170.4, 169.5, 150.7, 148.4, 145.3, 145.0, 136.9, 136.8, 130.7, 130.6, 122.0, 121.7, 120.5, 120.1, 117.4, 117.2, 115.9, 51.4, 47.8, 46.9, 44.0, 39.5, 26.7, 11.0<br>MS (ESI) [M + H]$^+$ = 446.4 |
| 2 | $^1$H NMR (300 MHz, MeOD) δ 8.38 (dd, J = 5.0, 1.5 Hz, 2H), 7.85 (dd, J = 5.0, 1.5 Hz, 2H), 7.78 (d, J = 8.8 Hz, 2H), 7.76 (s, 1H), 7.52-7.44 (m, 1H), 7.39-7.34 (m, 2H), 7.12 (d, J = 8.8 Hz, 2H), 3.44 (t, J = 6.4 Hz, 2H), 3.15-3.03 (m, 6H), 2.02 (q, J = 6.4 Hz, 2H), 1.25 (t, J = 7.3 Hz, 6H) |
| 3 | $^1$H NMR (300 MHz, MeOD) δ 8.41 (dd, J = 5.1, 1.5 Hz, 2H), 7.90 (dd, J = 5.1, 1.5 Hz, 2H), 7.66 (d, J = 6.7 Hz, 2H), 7.44-7.23 (m, 7H), 3.90 (t, J = 4.7 Hz, 4H), 3.47 (t, J = 6.4 Hz, 2H), 3.20-2.99 (m, 6H), 2.08 (q, J = 14.0, 6.9 Hz, 2H)<br>MS (ESI) [M + H]$^+$ = 460.2 |
| 4 | $^1$H NMR (300 MHz, MeOD) δ 8.43 (dd, J = 5.0, 1.6 Hz, 2H), 7.83 (dd, J = 4.9, 1.6 Hz, 2H), 7.66 (t, J = 2.1 Hz, 1H), 7.59 (t, J = 2.1 Hz, 1H), 7.43 (t, J = 1.8 Hz, 1H), 7.39 (d, J = 6.8 Hz, 1H), 7.37-7.25 (m, 4H), 3.42 (t, J = 6.9 Hz, 2H), 2.68-2.53 (m, 6H), 1.90-1.75 (m, 6H)<br>$^{13}$C NMR (75 MHz, MeOD) δ 170.2, 169.3, 150.7, 148.3, 145.2, 144.8, 136.8, 136.7, 130.6, 130.5, 122.0, 121.6, 120.3, 120.0, 117.2, 117.1, 115.7, 55.1, 54.9, 39.4, 29.2, 24.1<br>MS (ESI) [M + H]$^+$ = 444.4 |
| 5 | $^1$H NMR (300 MHz, MeOD) δ 8.40 (d, J = 6.3 Hz, 2H), 7.81 (d, J = 6.5 Hz, 2H), 7.69 (d, J = 1.4 Hz, 1H), 7.59 (t, J = 1.8 Hz, 1H), 7.47 (d, J = 7.6 Hz, 1H), 7.40 (dt, J = 7.6, 4.0 Hz, 2H), 7.31 (m, 3H), 2.93 (t, J = 6.6 Hz, 2H), 2.46 (q, J = 7.3 Hz, 6H), 1.67-1.51 (q, J = 6.7 Hz, 2H), 0.97 (t, J = 7.2 Hz, 6H)<br>$^{13}$C NMR (75 MHz, MeOD) δ 169.3, 150.9, 148.5, 145.8, 144.7, 142.9, 136.9, 131.4, 130.9, 122.9, 121.8, 121.2, 119.4, 118.0, 115.9, 115.6, 51.3, 47.8, 43.0, 27.1, 11.4<br>MS (ESI) [M + H]$^+$ = 482.2 |
| 6 | $^1$H NMR (300 MHz, MeOD) δ 8.40 (dd, J = 5.1, 1.4 Hz, 2H), 7.82 (dd, J = 4.9, 1.5 Hz, 2H), 7.65 (s, 1H), 7.58 (s, 1H), 7.45-7.24 (m, 6H), 3.40 (t, J = 6.7 Hz, 2H), 2.70-2.31 (m, 10H), 2.26 (s, 3H), 1.85-1.73 (m, 2H).<br>$^{13}$C NMR (75 MHz, MeOD) δ 170.4, 169.5, 150.8, 148.5, 145.4, 145.0, 137.1, 136.9, 130.8, 130.7, 122.2, 121.7, 120.5, 120.2, 117.4, 117.3, 115.9, 57.4, 55.6, 53.6, 46.0, 39.7, 27.2<br>MS (ESI) [M + H]$^+$ = 473.2 |
| 7 | $^1$H NMR (300 MHz, MeOD) δ 8.40 (dd, J = 5.0, 1.3 Hz, 2H), 7.82 (dd, J = 5.0, 1.4 Hz, 2H), 7.65 (s, 1H), 7.59 (s, 1H), 7.49-7.15 (m, 6H), 3.38 (t, J = 6.8 Hz, 2H), 2.59-2.26 (m, 6H), 1.89-1.71 (m, 2H), 1.67-1.50 (m, 4H), 1.49-1.33 (m, 2H)<br>$^{13}$C NMR (75 MHz, MeOD) δ 170.4, 169.5, 150.7, 148.4, 145.4, 145.0, 137.0, 136.8, 130.7, 130.5, 122.1, 121.7, 120.4, 120.1, 117.1, 115.8, 58.0, 55.5, 39.6, 27.1, 26.5, 25.1<br>MS (ESI) [M + H]$^+$ = 458.2 |
| 8 | $^1$H NMR (300 MHz, MeOD) δ 8.42 (dd, J = 5.0, 1.4 Hz, 2H), 7.82 (dd, J = 4.9, 1.5 Hz, 2H), 7.68 (s, 1H), 7.48-7.26 (m, 4H), 7.25-7.10 (m, 2H), 6.90 (d, J = 7.4 Hz, 1H), 3.74 (s, 3H), 3.52 (s, 2H), 2.48 (s, 2H), 2.41 (s, 2H) |
| 9 | $^1$H NMR (300 MHz, MeOD) δ 8.43 (s, 2H), 7.83 (s, 2H), 7.71 (s, 1H), 7.59 (s, 1H), 7.54-7.26 (m, 6H), 3.02-2.83 (m, 2H), 2.55-2.14 (m, 6H), 1.73-1.62 (m, 2H), 1.61-1.48 (m, 4H), 1.46-1.34 (m, 2H)<br>MS (ESI) [M + H]$^+$ = 494.2 |
| 10 | $^1$H NMR (300 MHz, MeOD) δ 8.43 (dd, J = 4.9, 1.6 Hz, 2H), 7.83 (dd, J = 4.9, 1.6 Hz, 2H), 7.70 (t, J = 1.9 Hz, 1H), 7.60 (t, J = 1.9 Hz, 1H), 7.53-7.41 (m, 3H), 7.40-7.30 (m, 3H), 3.04 (t, J = 6.9 Hz, 2H), 2.44 (t, J = 6.9 Hz, 2H), 2.41-2.32 (m, 4H), 1.61-1.49 (m, 4H), 1.48-1.36 (m, 2H)<br>MS (ESI) [M + H]$^+$ = 480.1 |
| 11 | $^1$H NMR (300 MHz, CDCl$_3$) δ 9.18 (s, 1H), 8.61 (t, J = 4.5 Hz, 1H), 8.34 (d, J = 8.4 Hz, 1H), 8.20-8.13 (m, 1H), 7.73-7.66 (m, 1H), 7.60 (d, J = 7.1 Hz, 1H), 7.40-7.33 (m, 1H), 7.33-7.18 (m, 5H), 7.04-6.95 (m, 1H), 6.85 (s, 1H), 3.50 (dd, J = 11.1, 5.4 Hz, 2H), 2.72-2.50 (m, 6H), 1.87-1.71 (m, 2H), 1.03 (t, J = 7.2 Hz, 6H)<br>MS (ESI) [M + H]$^+$ = 446.3 |
| 12 | $^1$H NMR (300 MHz, MeOD) δ 8.44 (d, J = 6.3 Hz, 2H), 7.83 (d, J = 6.4 Hz, 2H), 7.71 (d, J = 1.6 Hz, 1H), 7.59 (d, J = 2.0 Hz, 1H), 7.53-7.45 (m, 1H), 7.43 (d, J = 7.6 Hz, 2H), 7.38-7.28 (m, 3H), 3.68-3.54 (m, 6H), 2.96 (t, J = 6.7 Hz, 2H), 2.42-2.27 (m, 6H), 1.64 (quint, J = 6.9 Hz, 2H).<br>$^{13}$C NMR (75 MHz, MeOD) δ 169.2, 150.7, 148.3, 145.9, 145.6, 144.5, 142.7, 131.3, 130.8, 122.8, 121.7, 121.1, 119.3, 117.8, 115.8, 115.4, 67.9, 57.3, 54.6, 42.6, 27.0<br>MS (ESI) [M + H]$^+$ = 496.1 |
| 13 | $^1$H NMR (300 MHz, MeOD) δ 8.40 (dd, J = 4.9, 1.5 Hz, 2H), 7.88 (dd, J = 6.9, 2.1 Hz, 2H), 7.82 (dd, J = 4.9, 1.6 Hz, 2H), 7.68-7.63 (m, 1H), 7.43-7.30 (m, 3H), 7.16 (dd, J = 6.9, 2.1 Hz, 2H), 3.40 (t, J = 6.8 Hz, 2H), 2.66-2.50 (m, 6H), 1.79 (qt, J = 6.8 Hz, 2H), 1.05 (t, J = 7.2 Hz, 6H) |
| 14 | $^1$H NMR (300 MHz, MeOD) δ 8.41 (dd, J = 4.9, 1.6 Hz, 2H), 7.88 (dd, J = 6.9, 2.1 Hz, 2H), 7.82 (dd, J = 4.9, 1.6 Hz, 2H), 7.66 (t, J = 2.1 Hz, 1H), 7.42-7.31 (m, 3H), 7.16 (dd, J = 6.9, 2.1 Hz, 2H), 3.68 (t, J = 4.5 Hz, 4H), 3.43 (t, J = 6.9 Hz, 2H), 2.53-2.42 (m, 6H), 1.83 (qt, J = 6.9 Hz, 2H) |
| 15 | $^1$H NMR (300 MHz, MeOD) δ 8.39 (dd, J = 5.0, 1.5 Hz, 2H), 7.90 (dd, J = 6.9, 1.8 Hz, 2H), 7.80 (dd, J = 5.0, 1.5 Hz, 2H), 7.65 (t, J = 1.8 Hz, 1H), 7.50-7.35 (m, 3H), 7.18 (dd, J = 6.9, 1.8 Hz, 2H), 3.66 (t, J = 4.5 Hz, 4H), 2.97 (t, J = 6.7 Hz, 2H), 2.49-2.34 (m, 6H), 1.67 (qt, J = 6.7 Hz, 2H) |
| 16 | $^1$H NMR (300 MHz, MeOD) δ 8.40 (dd, J = 4.9, 1.6 Hz, 2H), 7.91 (dd, J = 6.9, 2.1 Hz, 2H), 7.82 (dd, J = 4.9, 1.6 Hz, 2H), 7.68 (t, J = 1.8 Hz, 1H), 7.53-7.37 (m, 3H), 7.19 (dd, J = 6.9, 2.1 Hz, 2H), 3.08 (t, J = 6.7 Hz, 2H), 2.82-2.69 (m, 6H), 1.90-1.80 (m, 4H) |
| 17 | $^1$H NMR (300 MHz, MeOD) δ 8.41 (dd, J = 4.7, 1.6 Hz, 2H), 7.50 (t, J = 1.8 Hz, 1H), 7.32 (d, J = 7.9 Hz, 1H), 7.25 (d, J = 7.9 Hz, 1H), 7.21 (dd, J = 4.7, 1.6 Hz, 2H), 7.16 (dd, J = 7.5, 1.3 Hz, 1H), 7.11-7.05 (m, 2H), 6.87 (ddd, J = 7.4, 2.5, 1.3 Hz, 2H), 3.49 (s, 3H), 3.44 (t, J = 6.6 Hz, 2H), 3.03-2.90 (m, 6H), 2.02-1.90 (m, 2H), 1.20 (t, J = 7.3 Hz, 6H) |
| 18 | $^1$H NMR (300 MHz, MeOD) δ 8.41 (dd, J = 4.7, 1.6 Hz, 2H), 7.51-7.47 (m, 1H), 7.32 (d, J = 7.8 Hz, 1H), 7.25 (d, J = 7.9 Hz, 1H), 7.22 (dd, J = 4.7, 1.6 Hz, 2H), 7.16 (d, J = 7.5 Hz, 1H), 7.11-7.05 (m, 2H), 6.92-6.82 (m, 2H), 3.49 (s, 3H), 3.49-3.42 (m, 5H), 3.09-2.99 (m, 5H), 2.00-1.90 (m, 7H) |
| 19 | $^1$H NMR (300 MHz, MeOD) δ 8.42 (dd, J = 4.8, 1.5 Hz, 2H), 7.47 (t, J = 1.8 Hz, 1H), 7.36-7.25 (m, 2H), 7.22 (dd, J = 4.8, 1.5 Hz, 2H), 7.18 (d, J = 7.5 Hz, 1H), 7.14-7.08 (m, 2H), 6.96-6.87 (m, 2H), 3.49 (s, 3H), 2.95 (t, J = 7.1 Hz, 2H), 2.92-2.78 (m, 6H), 1.88-1.74 (m, 2H), 1.16 (t, J = 7.2 Hz, 6H) |
| 20 | $^1$H NMR (300 MHz, MeOD) δ 8.41 (dd, J = 4.7, 1.6 Hz, 2H), 7.45-7.42 (m, 1H), 7.26 (dd, J = 5.1, 3.4 Hz, 2H), 7.22 (dd, J = 4.7, 1.6 Hz, 2H), 7.17 (d, J = 7.5 Hz, 1H), 7.11-7.06 (m, 2H), 6.89 (dt, J = 6.8, 2.2 Hz, 1H), 6.85 (dt, J = 7.2, 1.5 Hz, 1H), 3.50 (s, 3H), 3.41 (t, J = 6.9 Hz, 2H), 2.74-2.33 (m, 10H), 2.29 (s, 3H), 1.81 (q, J = 6.9 Hz, 2H)<br>$^{13}$C NMR (75 MHz, MeOD) δ 172.7, 170.2, 154.1, 151.1, 144.9, 144.7, 137.5, 137.1, 130.5, 122.2, 121.4, 120.9, 120.7, 120.1, 117.6, 57.2, 55.5, 53.5, 45.8, 39.6, 37.7, 27.1<br>MS (ESI) [M + H]$^+$ = 487.5 |

TABLE II-continued

| Ex | Characterizations |
|---|---|
| 21 | ¹H NMR (300 MHz, MeOD) δ 8.41 (dd, J = 4.7, 1.6 Hz, 2H), 7.52 (t, J = 1.8 Hz, 1H), 7.34 (d, J = 7.6 Hz, 1H), 7.24 (d, J = 8.0 Hz, 1H), 7.20 (dd, J = 4.7, 1.6 Hz, 2H), 7.16 (dd, J = 7.5, 1.5 Hz, 1H), 7.11-7.05 (m, 2H), 6.92-6.81 (m, 2H), 3.48 (s, 3H), 3.48-3.39 (m, 2H), 3.08-2.87 (m, 6H), 2.12-1.97 (m, 2H), 1.88-1.71 (m, 4H), 1.63-1.50 (m, 2H) |
| 22 | ¹H NMR (300 MHz, MeOD) δ 8.41 (dd, J = 4.8, 1.6 Hz, 2H), 7.45 (t, J = 1.8 Hz, 1H), 7.27 (dd, J = 6.1, 4.5 Hz, 2H), 7.21 (dd, J = 4.7, 1.5 Hz, 2H), 7.16 (d, J = 7.5 Hz, 1H), 7.11-7.05 (m, 2H), 6.89 (dt, J = 7.5, 2.1 Hz, 1H), 6.85 (dt, J = 7.5, 1.2 Hz, 1H), 3.68 (t, J = 4.5 Hz, 4H), 3.49 (s, 3H), 3.42 (t, J = 6.8 Hz, 2H), 2.61-2.42 (m, 6H), 1.83 (qt, J = 6.8 Hz,, 2H) |
| 23 | ¹H NMR (300 MHz, MeOD) δ 8.43 (dd, J = 4.8, 1.5 Hz, 2H), 7.45 (t, J = 1.8 Hz, 1H), 7.34 (t, J = 7.7 Hz, 1H), 7.28 (dt, J = 7.8, 1.5 Hz, 1H), 7.23 (dd, J = 4.8, 1.5 Hz, 2H), 7.20 (d, J = 7.6 Hz, 1H), 7.15-7.07 (m, 2H), 6.97-6.88 (m, 2H), 3.67 (t, J = 4.5 Hz, 4H), 3.51 (s, 3H), 2.94 (t, J = 6.7 Hz, 2H), 2.55-2.38 (m, 6H), 1.68 (qt, J = 6.7 Hz,, 2H) |
| 24 | ¹H NMR (300 MHz, MeOD) δ 8.42 (dd, J = 4.8, 1.5 Hz, 2H), 7.46 (t, J = 1.8 Hz, 1H), 7.33 (t, J = 7.8 Hz, 1H), 7.28 (dt, J = 7.8, 1.4 Hz, 1H), 7.22 (dd, J = 4.8, 1.5 Hz, 2H), 7.19 (d, J = 7.6 Hz, 1H), 7.14-7.07 (m, 2H), 6.96-6.88 (m, 2H), 3.49 (s, 3H), 2.93 (t, J = 6.5 Hz, 2H), 2.80-2.61 (m, 6H), 1.87-1.75 (m, 2H), 1.69 (dt, J = 10.9, 5.5 Hz, 4H), 1.56-1.44 (m, 2H) |
| 25 | ¹H NMR (300 MHz, MeOD) δ 8.86 (d, J = 0.8 Hz, 1H), 8.64 (d, J = 5.9 Hz, 1H), 8.32 (d, J = 5.9, 1.3 Hz, 1H), 7.67 (t, J = 1.8 Hz, 1H), 7.58 (t, J = 1.8 Hz, 1H), 7.46 (t, J = 7.5, 1.5 Hz, 1H), 7.44-7.27 (m, 5H), 3.40 (t, J = 6.8 Hz, 2H), 2.70-2.60 (m, 6H), 1.87-1.76 (m, 2H), 1.07 (t, J = 7.2 Hz, 6H)<br>MS (ESI) [M + H]⁺ = 447.4 |
| 26 | ¹H NMR (300 MHz, MeOD) δ 8.87 (d, J = 0.8 Hz, 1H), 8.64 (dd, J = 5.9, 0.5 Hz, 1H), 8.32 (dd, J = 5.9, 1.3 Hz, 1H), 7.72 (t, J = 1.8 Hz, 1H), 7.58 (t, J = 1.8 Hz, 1H), 7.52 (dt, J = 7.5, 1.5 Hz, 2H), 7.48-7.40 (m, 2H), 7.40-7.30 (m, 3H), 2.95 (t, J = 6.6 Hz, 2H), 2.58-2.45 (m, 6H), 1.69-1.56 (m, 2H), 1.01 (t, J = 7.2 Hz, 6H) |
| 27 | ¹H NMR (300 MHz, MeOD) δ 8.85 (d, J = 0.8 Hz, 1H), 8.63 (d, J = 5.9 Hz, 1H), 8.30 (d, J = 5.9, 1.3 Hz, 1H), 7.72 (t, J = 1.8 Hz, 1H), 7.58 (t, J = 1.8 Hz, 1H), 7.51 (dt, J = 7.5, 1.5 Hz, 1H), 7.47-7.39 (m, 2H), 7.38-7.29 (m, 3H), 2.96 (t, J = 6.6 Hz, 2H), 2.68-2.52 (m, 6H), 1.78-1.68 (m, 2H), 1.67-1.58 (m, 4H), 1.55-1.44 (m, 2H) |
| 28 | ¹H NMR (300 MHz, MeOD) δ 8.83 (s, 1H), 8.62 (d, J = 5.9 Hz, 1H), 8.30 (dd, J = 5.9, 1.3 Hz, 1H), 7.66 (t, J = 1.6 Hz, 1H), 7.59 (t, J = 1.8 Hz, 1H), 7.49-7.39 (m, 1H), 7.39-7.21 (m, 4H), 3.41 (t, J = 6.8 Hz, 2H), 2.62 (t, J = 7.6 Hz, 6H), 2.00-1.65 (m, 6H) |
| 29 | ¹H NMR (300 MHz, MeOD) δ 8.87 (d, J = 0.8 Hz, 1H), 8.65 (d, J = 5.9 Hz, 1H), 8.33 (dd, J = 1.3, 5.9 Hz, 1H), 7.68 (t, J = 1.6 Hz, 1H), 7.58 (t, J = 1.7 Hz, 1H), 7.46 (t, J = 1.7 Hz, 1H), 7.41 (s, 1H), 7.38 (dd, J = 2.7, 4.4 Hz, 2H), 7.36-7.29 (m, 3H), 3.41 (t, J = 6.6 Hz, 2H), 2.57-2.45 (m, 6H), 1.91-1.79 (m, 2H), 1.66-1.57 (m, J = 5.4, 10.9, 6H), 1.55-1.44 (m, 2H) |
| 30 | ¹H NMR (300 MHz, MeOD) δ 8.86 (s, 1H), 8.64 (d, J = 5.6 Hz, 1H), 8.31 (d, J = 5.9 Hz, 1H), 7.67 (s, 1H), 7.59 (s, 1H), 7.51-7.25 (m, 6H), 3.74-3.66 (m, 4H), 3.43 (t, J = 6.7 Hz, 2H), 2.65-2.48 (m, 6H), 1.85 (quint, J = 7.0 Hz, 2H) |
| 31 | ¹H NMR (300 MHz, MeOD) δ 8.87 (s, 1H), 8.65 (d, J = 5.9, 1H), 8.32 (dd, J = 1.1, 5.9 Hz, 1H), 7.69 (s, 1H), 7.60 (s, 1H), 7.51-7.28 (m, 8H), 3.44 (t, J = 6.7 Hz, 2H), 2.72 (s, 8H), 2.60-2.52 (m, 2H), 2.44 (s, 3H), 1.91-1.77 (quint, J = 6.7, 2H)<br>¹³C NMR (75 MHz, MeOD) δ 170.4, 169.5, 160.0, 159.2, 158.8, 145.4, 144.9, 136.9, 136.2, 130.7, 130.6, 122.4, 121.8, 120.6, 120.2, 117.3, 117.2, 112.0, 56.8, 55.1, 52.9, 45.2, 39.3, 27.0.<br>MS (ESI) [M + H]⁺ = 474.4 |
| 32 | ¹H NMR (300 MHz, d₆-DMSO) δ 10.58 (s, 1H), 8.81 (s, 1H), 8.46 (d, J = 6.2, 4H), 7.85 (s, 1H), 7.77 (d, J = 4.9, 1H), 7.65 (s, 1H), 7.48 (dd, J = 7.9, 19.2, 2H), 7.36 (d, J = 8.3, 1H), 4.10 (dd, J = 4.9, 10.4, 2H), 3.00-2.85 (m, 6H), 1.71-1.53 (m, 2H), 0.92 (t, J = 7.0, 6H) |
| 33 | ¹H NMR (300 MHz, MeOD) δ 8.44 (dd, J = 4.9, 1.6 Hz, 2H), 8.25 (dd, J = 5.4, 0.7 Hz, 1H), 8.20 (t, J = 1.8 Hz, 1H), 7.86 (dd, J = 4.9, 1.6 Hz, 2H), 7.84-7.80 (m, 1H), 7.54-7.48 (m, 1H), 7.45 (d, J = 8.1 Hz, 1H), 7.32 (s, 1H), 7.10 (dd, J = 5.4, 1.5 Hz, 1H), 3.46 (t, J = 6.6 Hz, 2H), 3.00-2.85 (m, 6H), 2.00-1.87 (m, 2H), 1.20 (t, J = 7.3 Hz, 6H) |
| 34 | ¹H NMR (300 MHz, MeOD) δ 8.44 (dd, J = 1.6, 4.9 Hz, 2H), 8.26 (dd, J = 0.7, 5.4, 1H), 8.21 (t, J = 1.9, 1H), 7.84 (dd, J = 1.6, 4.9, 2H), 7.77 (ddd, J = 1.2, 2.3, 7.9, 1H), 7.52 (dt, J = 1.3, 7.7, 1H), 7.45 (t, J = 7.8, 1H), 7.21-7.18 (m, 1H), 7.07 (dd, J = 1.5, 5.4, 1H), 3.43 (t, J = 6.9, 2H), 2.65-2.44 (m, 10H), 2.30 (s, 3H), 1.83 (quint, J = 7.1, 2H). |
| 35 | ¹H NMR (300 MHz, MeOD) δ 8.72 (t, J = 1.7 Hz, 1H), 8.43 (dd, J = 5.0, 1.4 Hz, 2H), 7.87 (dd, J = 5.0, 1.5 Hz, 2H), 7.70 (dd, J = 8.3, 7.4 Hz, 1H), 7.58-7.38 (m, 4H), 6.98 (d, J = 7.8 Hz, 1H), 3.48 (t, J = 6.8 Hz, 2H), 2.60-2.41 (m, 6H), 1.81 (quint, J = 6.7 Hz, 2H), 0.94 (t, J = 7.2 Hz, 6H)<br>¹³C NMR (75 MHz, MeOD) δ 195.0, 169.2, 167.1, 156.1, 150.8, 148.5, 143.0, 139.7, 136.0, 130.0, 123.5, 121.0, 119.5, 115.8, 115.4, 114.3, 51.1, 47.6, 38.9, 27.1, 11.2<br>MS (ESI) [M + H]⁺ = 447.4 |
| 36 | ¹H NMR (300 MHz, MeOD) δ 8.42 (d, J = 6.4 Hz, 2H), 7.97 (d, J = 8.8 Hz, 2H), 7.84 (d, J = 6.4 Hz, 2H), 7.80-7.67 (m, 4H), 7.56 (d, J = 7.2 Hz, 1H), 7.05 (d, J = 7.7 Hz, 1H), 3.48 (t, J = 6.7 Hz, 2H), 2.73-2.41 (m, 6H), 1.92-1.70 (m, 2H), 1.02 (t, J = 7.2 Hz, 6H) |
| 37 | ¹H NMR (300 MHz, MeOD) δ 8.38 (dd, J = 1.6, 4.7 Hz, 2H), 8.08-8.02 (m, 1H), 7.67 (dd, J = 7.4, 8.3 Hz, 1H), 7.49 (dd, J = 0.8, 7.3, 1H), 7.39 (ddd, J = 0.9, 2.3, 8.2, 1H), 7.22 (dd, J = 1.6, 4.7, 2H), 7.16 (t, J = 7.9, 1H), 6.86 (dd, J = 0.8, 8.3, 1H), 6.83-6.76 (m, 1H), 3.53 (s, 3H), 3.49 (t, J = 6.9, 2H), 2.68-2.53 (m, 6H), 1.86 (quint, J = 6.9, 2H), 1.02 (t, J = 7.2, 6H) |
| 38 | ¹H NMR (300 MHz, MeOD) δ 8.38 (dd, J = 1.5, 4.8, 2H), 8.20 (d, J = 5.3, 1H), 7.99-7.92 (m, 1H), 7.56 (ddd, J = 0.8, 2.1, 8.2, 1H), 7.24 (dd, J = 1.5, 4.7, 3H), 7.19 (t, J = 7.9, 1H), 7.08 (dd, J = 1.4, 5.3, 1H), 6.91 (d, J = 7.9, 1H), 3.52 (s, 3H), 3.44 (t, J = 6.6, 2H), 2.87 (q, J = 7.3, 6H), 1.93 (quint, J = 6.9, 2H), 1.17 (t, J = 7.2, 6H) |
| 39 | ¹H NMR (300 MHz, MeOD) δ 8.39 (dd, J = 4.8, 1.5 Hz, 2H), 8.21 (d, J = 5.6 Hz, 1H), 7.96-7.89 (m, 1H), 7.54 (dd, J = 8.2, 1.3 Hz, 1H), 7.25 (dd, J = 4.8, 1.6 Hz, 2H), 7.21 (t, J = 8.0 Hz 1H), 7.15 (s, 1H), 7.06 (dd, J = 5.3, 1.4 Hz, 1H), 6.93 (d, J = 7.8 Hz, 1H), 3.53 (s, 3H), 3.44 (t, J = 6.8 Hz, 2H), 2.84-2.62 (m, 7H), 2.61-2.52 (m, 3H), 2.47 (s, 3H), 1.93-1.77 (m, 2H)<br>¹³C NMR (75 MHz, MeOD) δ 173.0, 168.5, 157.7, 154.1, 150.9, 149.1, 144.7, 142.8, 136.9, 129.8, 122.4, 122.2, 121.8, 119.7, 112.8, 110.2, 56.5, 55.0, 52.7, 45.2, 39.2, 37.8, 26.9<br>MS (ESI) [M + H]⁺ = 488.4 |
| 40 | ¹H NMR (300 MHz, MeOD) δ 8.92 (s, 1H), 8.82 (s, 1H), 8.34 (d, J = 5.2, 1H), 7.73 (d, J = 7.4, 8.3, 1H), 7.61-7.55 (m, 2H), 7.54 (d, J = 7.2, 1H), 7.46 (d, J = 1.7, 3.6, 2H), 7.02 (d, J = 8.3, 1H), 3.64 (d, J = 6.3, 2H), 3.20 (q, J = 7.2, 6H), 2.15-2.02 (m, 2H), 1.25 (t, J = 7.3, 6H) |
| 41 | ¹H NMR (300 MHz, MeOD) δ 8.83 (s, 1H), 8.62 (d, J = 5.9 Hz, 1H), 8.30 (dd, J = 5.9, 1.3 Hz, 1H), 8.26-8.20 (m, 2H), 7.78 (dd, J = 8.0, 1.2 Hz, 1H), 7.51 (d, J = 8.1 Hz, 1H), 7.40 (t, J = 7.9 Hz, 1H), 7.20 (s, 1H), 7.05 (dd, J = 5.3, 1.4 Hz, 1H), 3.41 (t, J = 6.8 Hz, 2H), 2.70 (q, J = 7.2 Hz, 6H), 1.84 (q, J = 7.5 Hz, 2H), 1.09 (q, J = 7.2 Hz, 6H)<br>¹³C NMR (75 MHz, MeOD) δ 169.5, 168.5, 160.0, 159.2, 158.7, 157.8, 149.1, 144.8, 142.9, 135.7, 130.2, 124.1, 121.9, 119.3, 112.9, 111.9, 110.3, 51.2, 47.8, 39.3, 26.5, 10.8<br>MS (ESI) [M + H]⁺ = 448.5 |
| 42 | ¹H NMR (300 MHz, CDCl₃) δ 9.46 (s, 1H), 8.79 (s, 1H), 8.64 (s, 1H), 8.61 (d, J = 5.9 Hz, 1H), 8.29 (d, J = 5.7 Hz, 1H), 8.22 (d, J = 5.2, 1H), 8.18 (d, J = 5.4, 2H), 7.80 (d, J = 7.8 Hz, 1H), 7.45 (d, J = 7.7, 1H), 7.36 (d, J = 6.8, 2H), 6.97 (d, J = 5.1, 1H), 3.58-3.45 (m, J = 4.9, 2H), 2.66-2.34 (m, 10H), 2.24 (s, 3H), 1.84-1.64 (m, J = 5.0, 2H) |
| 43 | ¹H NMR (300 MHz, MeOD) δ 8.41 (dd, J = 1.6, 4.9 Hz, 2H), 8.35 (d, J = 5.2, 1H), 8.20 (s, 1H), 7.87 (dd, J = 1.6, 4.9, 2H), 7.85 (s, 1H), 7.81-7.73 (m, 1H), 7.58 (dd, J = 0.9, 7.3, 1H), 7.33 (dd, J = 1.6, 5.3, 1H), 3.45 (t, J = 6.7, 2H), 2.72 (q, J = 7.2, 6H), 1.90 (quint, J = 6.7, 2H), 1.07 (t, J = 7.2, 6H) |
| 44 | ¹H NMR (300 MHz, d₆-DMSO) δ 10.86 (s, 1H), 10.16 (s, 1H), 8.76 (t, J = 5.3 Hz, 1H), 8.51 (d, J = 6.3 Hz, 2H), 8.44 (d, J = 5.2 Hz, 1H), 8.36 (d, J = 5.2 Hz, 2H), 8.20 (s, 1H), 8.10 (s, 1H), 7.80 (d, J = 6.3 Hz, 2H), 7.36 (d, J = 5.2, 1.2 Hz, 1H), 7.23 (dd, J = 5.2, 1.1 Hz, 1H), 3.30 (dd, J = 12.1, 6.5 Hz, 3H), 2.57-2.43 (m, 8H), 1.74-1.62 (m, 2H), 0.96 (t, J = 7.1 Hz, 7H) |

TABLE II-continued

| Ex | Characterizations |
|---|---|
| | $^{13}$C NMR (75 MHz, DMSO) δ 175.2, 174.7, 164.3, 164.2, 159.9, 157.8, 157.5, 155.0, 153.3, 152.7, 123.6, 123.2, 123.0, 119.7, 119.7, 59.5, 55.7, 47.5, 35.5, 20.9<br>MS (ESI) [M + H]$^+$ = 448.4 |
| 45 | $^1$H NMR (300 MHz, MeOD) δ 8.47 (d, J = 6.4, 2H), 8.42 (d, J = 5.3, 1H), 8.36 (d, J = 5.2, 1H), 8.12 (s, 1H), 8.01 (s, 1H), 7.85 (d, J = 6.5, 2H), 7.33 (dd, J = 1.3, 5.2, 1H), 7.21 (dd, J = 1.4, 5.2, 1H), 3.73 (t, J = 6.6, 2H), 3.45 (t, J = 6.8, 2H), 2.63-2.41 (m, 6H), 2.28 (s, 3H), 1.92-1.78 (m, 4H) |
| 46 | $^1$H NMR (300 MHz, MeOD) δ 8.45 (dd, J = 1.6, 4.9, 2H), 8.39 (t, J = 1.8, 1H), 8.34 (dd, J = 0.6, 5.3, 1H), 7.83 (dd, J = 1.6, 4.9, 2H), 7.81-7.77 (m, 1H), 7.45 (t, J = 7.8, 1H), 7.41 (t, J = 1.5, 1H), 7.27 (s, 1H), 7.21 (dd, J = 1.5, 5.3, 1H), 2.96 (t, J = 6.7, 2H), 2.56-2.44 (m, 6H), 1.62 (quint, J = 6.9, 2H), 0.99 (t, J = 7.2, 6H) |
| 47 | $^1$H NMR (300 MHz, MeOD) δ 8.41 (dd, J = 1.5, 5.0, 2H), 8.25 (d, J = 5.3, 1H), 8.10 (s, 1H), 7.82 (dd, J = 1.5, 5.0, 2H), 7.76 (dt, J = 2.1, 6.9, 1H), 7.37-7.29 (m, 3H), 7.15 (dd, J = 1.4, 5.3, 1H), 3.40 (t, J = 6.7, 2H), 2.73-2.61 (m, J = 3.1, 7.2, 6H), 1.82 (quint, J = 6.7, 2H), 1.07 (t, J = 7.2, 6H)<br>$^{13}$C NMR (75 MHz, MeOD) δ 170.7, 167.7, 158.0, 150.9, 149.4, 148.1, 144.6, 142.9, 136.5, 130.1, 123.2, 121.3, 119.0, 116.0, 113.1, 110.6, 51.4, 47.9, 39.5, 26.8, 11.1<br>MS (ESI) [M + H]$^+$ = 447.4 |
| 48 | $^1$H NMR (300 MHz, MeOD) δ 8.46 (d, J = 6.1, 2H), 8.31 (d, J = 5.3, 1H), 8.12 (s, 1H), 8.01 (d, J = 7.0, 1H), 7.84 (d, J = 6.6, 2H), 7.79-7.71 (m, 1H), 7.39 (d, J = 5.1, 2H), 7.27 (s, 1H), 7.19 (d, J = 5.3, 1H), 6.81 (d, J = 6.9, 1H), 3.70 (t, J = 4.7, 4H), 3.45 (t, J = 6.9, 2H), 2.60-2.48 (m, 6H), 1.86 (quint, J = 6.9, 2H) |
| 49 | $^1$H NMR (300 MHz, MeOD) δ 8.46 (dd, J = 1.5, 5.0, 2H), 8.31 (d, J = 5.3, 1H), 8.15-8.10 (m, J = 1.1, 1H), 7.84 (dd, J = 1.5, 5.0, 2H), 7.80-7.73 (m, 1H), 7.41-7.37 (m, 2H), 7.28 (s, 1H), 7.19 (dd, J = 1.5, 5.3, 1H), 3.44 (t, J = 6.7, 2H), 2.70-2.58 (m, 6H), 1.96-1.84 (m, 2H), 1.72-1.62 (m, J = 5.4, 11.0, 4H), 1.57-1.48 (m, J = 5.0, 2H) |
| 50 | $^1$H NMR (300 MHz, CDCl$_3$) δ 10.07 (s, 1H), 8.97 (t, J = 4.9, 1H), 8.45 (d, J = 6.2, 2H), 8.16 (d, J = 5.2, 1H), 7.87 (s, 1H), 7.75 (d, J = 6.2, 2H), 7.70 (s, 1H), 7.57 (d, J = 6.8, 1H), 7.25-7.18 (m, J = 5.9, 3H), 7.07 (d, J = 5.2, 1H), 3.53-3.42 (m, J = 5.2, 10.8, 2H), 2.73 (t, J = 5.9, 2H), 2.64 (s, 4H), 1.79 (s, 6H) |
| 51 | $^1$H NMR (300 MHz, CDCl$_3$) δ 10.17 (s, 1H), 8.64-8.56 (m, J = 4.7, 1H), 8.45 (d, J = 6.3, 2H), 8.15 (d, J = 5.2, 1H), 7.87 (s, 1H), 7.81-7.72 (m, 3H), 7.64-7.56 (m, 1H), 7.23 (d, J = 17.1, 2H), 7.07 (d, J = 4.8, 1H), 3.53-3.42 (m, J = 5.2, 11.3, 2H), 2.52 (dd, J = 8.5, 13.9, 10H), 2.21 (s, 3H), 1.78-1.65 (m, 2H)<br>$^{13}$C NMR (75 MHz, MeOD) δ 170.6, 167.8, 158.1, 151.0, 149.5, 148.1, 144.9, 142.9, 136.8, 130.2, 123.3, 121.4, 119.1, 116.0, 113.1, 110.5, 57.5, 55.8, 53.8, 46.1, 39.8, 27.2<br>MS (ESI) [M + H]$^+$ = 474.5 |

Among said compounds of formula (I), compounds (1), (3), (4), (5), (6), (7), (9), (10), (12), (20), (25), (28), (29), (30), (31), (34), (35), (40), (41), (42), (44), (45), (48), (49), and (51), or one of their pharmaceutically acceptable salts are of particular interest.

The following examples illustrate in detail the preparation of compounds (1), (4), (5), (6) (7), (20), (25), (31), (35), (39), (41), (44), (47) and (51) according to the invention. The structures of the products obtained have been confirmed at least by NMR spectra.

EXAMPLES

Example 1: Compound (1) in Table I

According to route (B), 4-aminopyridine (4.2 g, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-nitrobenzoyl chloride (7.4 g, 40 mmoles, 1 eq.) in dichloromethane (40 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (2.5 g, 26%).

$^1$H NMR (300 MHz, d$_6$-DMSO) δ 10.91 (s, 1H), 8.80 (s, 1H), 8.52 (d, J=5.5 Hz, 2H), 8.47 (d, J=7.9 Hz, 1H), 8.41 (d, J=7.9 Hz, 1H), 7.86 (t, J=7.9 Hz, 1H), 7.79 (d, J=5.3 Hz, 2H).

According to route (C), 3-nitro-N-(pyridin-4-yl)benzamide (1.5 g, 6.2 mmoles, 1 eq.) and 10% Pd/C (250 mg) were placed in EtOH (50 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyridin-4-yl)benzamide (1.24 g, 94%).

$^1$H NMR (300 MHz, d$_6$-DMSO) δ 10.44 (s, 1H), 8.44 (d, J=6.3 Hz, 2H), 7.77 (d, J=6.3 Hz, 2H), 7.18 (t, J=7.9 Hz, 1H), 7.12-7.03 (m, 2H), 6.78 (d, J=7.9 Hz, 1H), 5.38 (s, 2H).

N,N-diethylpropylenediamine (8.7 mL, 55 mmoles, 1.1 eq.) was placed in a 3N NaOH aqueous solution (71 mL) and dichloromethane (30 mL) was added to the solution. The reaction mixture was cooled down to 0° C. with an ice bath and a solution of 3-bromobenzoyl chloride (6.6 mL, 50 mmoles, 1 eq.) in dichloromethane (50 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-diethylamino-propyl)benzamide (15.6 g, 100%).

$^1$H NMR (300 MHz, CDCl$_3$) δ 9.15 (br s, 1H), 7.91 (s, 1H), 7.75 (d, J=7.9 Hz, 1H), 7.58 (d, J=7.9 Hz, 1H), 7.29 (t, J=7.9 Hz, 1H), 3.56 (dd, J=10.3, 5.8 Hz, 2H), 2.67-2.53 (m, 6H), 1.74 (quint, J=5.7 Hz, 2H), 1.04 (t, J=7.1 Hz, 6H).

According to route (A), a reaction mixture of 3-bromo-N-(3-diethylamino-propyl)benzamide (291 mg, 0.9 mmole, 1 eq.), 3-amino-N-(pyridin-4-yl)benzamide (300 mg, 1.4 mmole, 1.5 eq.), Pd$_2$(dba)$_3$ (42 mg, 0.046 mmole, 5 mol %), XPhos (44 mg, 0.09 mmole, 10 mol %) and K$_2$CO$_3$ (514 mg, 3.72 mmoles, 4 eq.) in t-BuOH (4 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-(3-(diethylamino)propyl)-3-((3-(pyridin-4-ylcarbamoyl)phenyl)amino)benzamide (1) (230 mg, 57%).

Example 2: Compound (4) in Table I

According to route (B), 4-aminopyridine (4.2 g, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-nitrobenzoyl chloride (7.4 g, 40 mmoles, 1 eq.) in dichloromethane (40 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (2.5 g, 26%).

$^1$H NMR (300 MHz, d$_6$-DMSO) δ 10.91 (s, 1H), 8.80 (s, 1H), 8.52 (d, J=5.5 Hz, 2H), 8.47 (d, J=7.9 Hz, 1H), 8.41 (d, J=7.9 Hz, 1H), 7.86 (t, J=7.9 Hz, 1H), 7.79 (d, J=5.3 Hz, 2H).

According to route (C), 3-nitro-N-(pyridin-4-yl)benzamide (994 mg, 4.1 mmoles, 1 eq.) and 10% Pd/C (218 mg) were placed in EtOH (20.5 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyridin-4-yl)benzamide (900 mg, 100%).

$^1$H NMR (300 MHz, d$_6$-DMSO) δ 10.42 (s, 1H), 8.44 (d, J=6.3 Hz, 2H), 7.75 (d, J=6.3 Hz, 2H), 7.16 (t, J=7.9 Hz, 1H), 7.10-7.01 (m, 2H), 6.76 (d, J=7.9 Hz, 1H), 5.36 (s, 2H).

3-(pyrrolidin-1-yl)propylamine (1.4 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-pyrrolidin-1-yl-propyl)benzamide (2.9 g, 94%).

$^1$H NMR (300 MHz, CDCl$_3$) δ 9.19 (s, 1H), 7.82 (s, 1H), 7.77 (d, J=7.9 Hz, 1H), 7.58 (d, J=7.9 Hz, 1H), 7.29 (t, J=7.9 Hz, 1H), 3.57 (dd, J=9.4, 4.8 Hz, 2H), 2.72 (t, J=4.8 Hz, 2H), 2.58 (s, 4H), 1.86 (s, 4H), 1.78 (t, J=4.8 Hz, 2H).

According to route (A), a reaction mixture of 3-bromo-N-(3-diethylamino-propyl)benzamide (611 mg, 1.97 mmole, 1 eq.), 3-amino-N-(pyridin-4-yl)benzamide (630 mg, 2.96 mmoles, 1.5 eq.), Pd$_2$(dba)$_3$ (90 mg, 0.095 mmole, 5 mol %), XPhos (94 mg, 0.19 mmole, 10 mol %) and K$_2$CO$_3$ (1.1 g, 7.88 mmoles, 4 eq.) in t-BuOH (8 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-(pyridin-4-yl)-3-((3-((3-(pyrrolidin-1-yl)propyl)carbamoyl)phenyl)amino)benzamide (4) (427 mg, 49%).

Example 3: Compound (5) in Table I

According to route (B), 4-aminopyridine (4.2 g, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-nitrobenzoyl chloride (7.4 g, 40 mmoles, 1 eq.) in dichloromethane (40 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (994 mg, 20%).

$^1$H NMR (300 MHz, d$_6$-DMSO) δ 10.91 (s, 1H), 8.80 (s, 1H), 8.52 (d, J=5.5 Hz, 2H), 8.47 (d, J=7.9 Hz, 1H), 8.41 (d, J=7.9 Hz, 1H), 7.86 (t, J=7.9 Hz, 1H), 7.79 (d, J=5.3 Hz, 2H).

According to route (C), 3-nitro-N-(pyridin-4-yl)benzamide (994 mg, 4.1 mmoles, 1 eq.) and 10% Pd/C (218 mg) were placed in EtOH (20.5 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyridin-4-yl)benzamide (900 mg, 100%).

$^1$H NMR (300 MHz, d$_6$-DMSO) δ 10.42 (s, 1H), 8.44 (d, J=6.3 Hz, 2H), 7.75 (d, J=6.3 Hz, 2H), 7.16 (t, J=7.9 Hz, 1H), 7.10-7.01 (m, 2H), 6.76 (d, J=7.9 Hz, 1H), 5.36 (s, 2H).

3-Bromobenzenesulfonyl chloride (0.56 mL, 3.9 mmoles, 1 eq.) and N,N-diisopropylethylamine (1.02 mL, 5.9 mmoles, 1.5 eq.) were placed in anhydrous dichloromethane (20 mL). The reaction mixture was cooled down to 0° C. with an ice bath and N,N-diethylpropylenediamine (1.23 mL, 7.8 mmoles, 2 eq.) was added dropwise. The reaction mixture was then stirred at 0° C. for 2 hours under an inert atmosphere of argon. The mixture was washed with saturated aqueous solutions of NH$_4$Cl and then NaCl. The aqueous phases were extracted with dichloromethane. The organic phases were gathered, dried over MgSO$_4$, filtered and concentrated under reduced pressure to afford 3-bromo-N-(3-diethylaminopropyl)benzenesulfonamide (524 mg, 38%).

$^1$H NMR (300 MHz, CDCl$_3$) δ 7.98 (s, 1H), 7.78 (d, J=7.9 Hz, 1H), 7.66 (d, J=8.0 Hz, 1H), 7.37 (t, J=7.9 Hz, 1H), 3.05 (t, J=5.4 Hz, 2H), 2.63-2.47 (m, 6H), 1.68 (t, J=5.4 Hz, 2H), 1.06 (t, J=7.1 Hz, 6H).

According to route (A), a reaction mixture of 3-bromo-N-(3-diethylaminopropyl)benzenesulfonamide (153 mg, 0.44 mmole, 1 eq.), 3-amino-N-(pyridin-4-yl)benzamide (103 mg, 0.48 mmole, 1.1 eq.), Pd$_2$(dba)$_3$ (20 mg, 0.022 mmole, 5 mol %), XPhos (21 mg, 0.044 mmole, 10 mol %) and K$_2$CO$_3$ (243 mg, 1.76 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give 3-((3-(N-(3-(diethylamino)propyl)sulfamoyl)phenyl)amino)-N-(pyridin-4-yl)benzamide (5) (97 mg, 46%).

Example 4: Compound (6) in Table I

According to route (B), 4-aminopyridine (2.1 g, 22 mmoles, 1.1 eq.) was placed in a 3N NaOH aqueous solution (28 mL) and dichloromethane (12 mL) was added to the solution. The reaction mixture was cooled down to 0° C. with an ice bath and a solution of 3-nitrobenzoyl chloride (3.7 g, 20 mmoles, 1 eq.) in dichloromethane (20 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (2.4 g, 50%).

$^1$H NMR (300 MHz, d$_6$-DMSO) δ 10.98 (s, 1H), 8.80 (s, 1H), 8.51 (d, J=6.2 Hz, 2H), 8.47 (d, J=7.9 Hz, 1H), 8.42 (d, J=7.9 Hz, 1H), 7.86 (t, J=7.9 Hz, 1H), 7.80 (d, J=6.2 Hz, 2H).

According to route (C), 3-nitro-N-(pyridin-4-yl)benzamide (1 g, 4.1 mmoles, 1 eq.) and 10% Pd/C (150 mg) were placed in EtOH (30 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyridin-4-yl)benzamide (660 mg, 75%).

¹H NMR (300 MHz, DMSO) δ 10.46 (s, 1H), 8.45 (dd, J=5.0, 1.3 Hz, 2H), 7.77 (dd, J=5.0, 1.3 Hz, 2H), 7.17 (t, J=7.9 Hz, 1H), 7.12-7.03 (m, 2H), 6.77 (dd, J=7.9, 1.2 Hz, 1H), 5.38 (s, 2H).

3-(4-methylpiperazin-1-yl)propylamine (1.9 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over MgSO₄, filtered and concentrated under reduced pressure to afford 3-bromo-N-(4-methylpiperazin-1-yl-propyl)benzamide (2.7 g, 80%).

¹H NMR (300 MHz, CDCl₃) δ 8.61 (br s, 1H), 7.92 (s, 1H), 7.82 (d, J=7.9 Hz, 1H), 7.62 (d, J=7.9 Hz, 1H), 7.32 (t, J=7.9 Hz, 1H), 3.57 (q, J=5.2 Hz, 2H), 2.79-2.35 (m, 10H), 2.33 (s, 3H), 1.78 (quint, J=5.2 Hz, 2H).

According to route (A), a reaction mixture of 3-bromo-N-(4-methylpiperazin-1-yl-propyl)benzamide (170 mg, 0.5 mmole, 1 eq.), 3-amino-N-(pyridin-4-yl)benzamide (117 mg, 0.55 mmole, 1.1 eq.), Pd₂(dba)₃ (23 mg, 0.025 mmole, 5 mol %), XPhos (24 mg, 0.05 mmole, 10 mol %) and K₂CO₃ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO₄, filtered and concentrated under reduced pressure. The resulting residue was purified by column chromatography on silica gel to give N-(3-(4-methylpiperazin-1-yl)propyl)-3-((3-(pyridin-4-ylcarbamoyl)phenyl)amino)benzamide (6) (52 mg, 22%).

Example 5: Compound (7) in Table I

According to route (B), 4-aminopyridine (4.2 g, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-nitrobenzoyl chloride (7.4 g, 40 mmoles, 1 eq.) in dichloromethane (40 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (2.5 g, 26%).

¹H NMR (300 MHz, d₆-DMSO) δ 10.91 (s, 1H), 8.80 (s, 1H), 8.52 (d, J=5.5 Hz, 2H), 8.47 (d, J=7.9 Hz, 1H), 8.41 (d, J=7.9 Hz, 1H), 7.86 (t, J=7.9 Hz, 1H), 7.79 (d, J=5.3 Hz, 2H).

According to route (C), 3-nitro-N-(pyridin-4-yl)benzamide (1.5 g, 6.2 mmoles, 1 eq.) and 10% Pd/C (250 mg) were placed in EtOH (50 mL). The reaction mixture was stirred at room temperature for 16 hours under an atmosphere of H₂. The reaction mixture was then filtered on celite, washed with EtOH and the filtrate was concentrated under reduced pressure to afford 3-amino-N-(pyridin-4-yl) benzamide (1.24 g, 94%).

¹H NMR (300 MHz, d₆-DMSO) δ 10.44 (s, 1H), 8.44 (d, J=6.3 Hz, 2H), 7.77 (d, J=6.3 Hz, 2H), 7.18 (t, J=7.9 Hz, 1H), 7.12-7.03 (m, 2H), 6.78 (d, J=7.9 Hz, 1H), 5.38 (s, 2H).

3-(piperidin-1-yl)propylamine (1.7 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over MgSO₄, filtered and concentrated under reduced pressure to afford 3-bromo-N-(piperidin-1-yl-propyl)benzamide (3.24 g, 100%).

¹H NMR (300 MHz, CDCl₃) δ 9.02 (s, 1H), 7.97 (s, 1H), 7.83 (d, J=7.9 Hz, 1H), 7.60 (d, J=7.9 Hz, 1H), 7.31 (t, J=7.9 Hz, 1H), 3.56 (dd, J=9.8, 4.8 Hz, 2H), 2.53 (t, J=4.8 Hz, 2H), 2.44 (s, 4H), 1.76 (t, J=4.8 Hz, 2H), 1.62 (t, J=4.8 Hz, 4H), 1.50 (s, 2H).

According to route (A), a reaction mixture of 3-bromo-N-(piperidin-1-yl-propyl)benzamide (162 mg, 0.5 mmole, 1 eq.), 3-amino-N-(pyridin-4-yl)benzamide (117 mg, 0.55 mmole, 1.1 eq.), Pd₂(dba)₃ (23 mg, 0.025 mmole, 5 mol %), XPhos (24 mg, 0.05 mmole, 10 mol %) and K₂CO₃ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO₄, filtered and concentrated under reduced pressure. The resulting residue was purified by column chromatography on silica gel to give N-(3-(piperidin-1-yl)propyl)-3-((3-(pyridin-4-ylcarbamoyl)phenyl)amino)benzamide (7) (115 mg, 50%).

Example 6: Compound (20) in Table I

According to route (D), a reaction mixture of 4-(methylamino)pyridine (1.25 g, 11.6 mmoles, 1.0 eq.), 3-nitrobenzoyl chloride (2.57 g, 13.9 mmoles, 1.2 eq.), N,N-diisopropylethylamine (3.02 mL, 17.3 mmoles, 1.5 eq.) and dimethylaminopyridine (103 mg, 1.41 mmole, 1 eq.) in dichloromethane (25 mL) was stirred at room temperature for 18 hours under an inert atmosphere of argon. The organic phase was washed with water, dried over MgSO₄, filtered and concentrated under reduced pressure. The resulting residue was purified by column chromatography on silica gel to give N-methyl-3-nitro-N-(pyridin-4-yl)benzamide (2.96 g, 100%).

¹H NMR (300 MHz, CDCl₃) δ 8.50 (dd, J=4.6, 1.6 Hz, 2H), 8.25 (s, 1H), 8.21 (d, J=7.9 Hz, 1H), 7.62 (d, J=7.9 Hz, 1H), 7.45 (t, J=7.9 Hz, 1H), 6.98 (dd, J=4.6, 1.6 Hz, 2H), 3.56 (s, 3H).

According to route (C), N-methyl-3-nitro-N-(pyridin-4-yl)benzamide (2.96 g, 11.5 mmoles, 1 eq.) and 10% Pd/C (450 mg) were placed in EtOH (100 mL). The reaction mixture was stirred at room temperature for 16 hours under an atmosphere of H₂. The reaction mixture was then filtered on celite, washed with EtOH and the filtrate was concentrated under reduced pressure to afford 3-amino-N-methyl-N-(pyridin-4-yl)benzamide (2.5 g, 96%).

¹H NMR (300 MHz, d₆-DMSO) δ 8.40 (dd, J=4.6, 1.6 Hz, 2H), 7.14 (dd, J=4.6, 1.6 Hz, 2H), 6.89 (t, J=7.9 Hz, 1H), 6.59 (s, 1H), 6.53 (d, J=7.9 Hz, 1H), 6.34 (d, J=7.9 Hz, 1H), 5.22 (s, 2H), 3.37 (s, 3H).

3-(4-methylpiperazin-1-yl)propylamine (1.9 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(4-methylpiperazin-1-yl-propyl)benzamide (2.7 g, 80%).

$^1$H NMR (300 MHz, CDCl$_3$) δ 8.61 (br s, 1H), 7.92 (s, 1H), 7.82 (d, J=7.9 Hz, 1H), 7.62 (d, J=7.9 Hz, 1H), 7.32 (t, J=7.9 Hz, 1H), 3.57 (q, J=5.2 Hz, 2H), 2.79-2.35 (m, 10H), 2.33 (s, 3H), 1.78 (quint, J=5.2 Hz, 2H).

According to route (A), a reaction mixture of 3-bromo-N-(4-methylpiperazin-1-yl-propyl)benzamide (170 mg, 0.5 mmole, 1 eq.), 3-amino-N-methyl-N-(pyridin-4-yl)benzamide (125 mg, 0.55 mmole, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-methyl-3-((3-((3-(4-methylpiperazin-1-yl)propyl)carbamoyl)phenyl)amino)-N-(pyridin-4-yl)benzamide (20) (34 mg, 14%).

Example 7: Compound (25) in Table I

According to route (E), a reaction mixture of 4-aminopyrimidine (885 mg, 9.3 mmoles, 1.1 eq.), 3-nitrobenzoic acid (1.4 g, 8.4 mmoles, 1 eq.), EDCI.HCl (2.4 g, 12.6 mmoles, 1.5 eq.), triethylamine (1.3 mL, 9.3 mmoles, 1.1 eq.) and dimethylaminopyridine (103 mg, 0.8 mmole, 0.1 eq.) in dichloromethane (10 mL) was stirred at room temperature for 18 hours under an inert atmosphere of argon. The resulting precipitate was filtered and washed with water and dichloromethane. The organic filtrate was concentrated under reduced pressure and the resulting residue was purified by column chromatography on silica gel. The former precipitate and the purified compound were gathered to afford 3-nitro-N-(pyrimidin-4-yl)benzamide (1.35 g, 66%).

$^1$H NMR (300 MHz, d$_6$-DMSO) δ 11.69 (s, 1H), 8.99 (s, 1H), 8.83 (s, 1H), 8.76 (d, J=5.6 Hz, 1H), 8.50-8.40 (m, 2H), 8.22 (dt, J=5.6, 1.2 Hz, 1H), 7.83 (t, J=7.9 Hz, 1H).

According to route (C), 3-nitro-N-(pyrimidin-4-yl)benzamide (1.35 g, 5.5 mmoles, 1 eq.) and 10% Pd/C (303 mg) were placed in EtOH (30 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyrimidin-4-yl)benzamide (1.2 g, 100%).

$^1$H NMR (300 MHz, d$_6$-DMSO) δ 10.93 (br s, 1H), 8.92 (dd, J=1.3, 0.5 Hz, 1H), 8.69 (dd, J=5.8, 0.5 Hz, 1H), 8.18 (dd, J=5.8, 1.3 Hz, 1H), 7.20-7.12 (m, 3H), 6.78 (dt, J=4.1, 2.3 Hz, 1H), 5.35 (s, 2H).

N,N-diethylpropylenediamine (8.7 mL, 55 mmoles, 1.1 eq.) was placed in a 3N NaOH aqueous solution (71 mL) and dichloromethane (30 mL) was added to the solution. The reaction mixture was cooled down to 0° C. with an ice bath and a solution of 3-bromobenzoyl chloride (6.6 mL, 50 mmoles, 1 eq.) in dichloromethane (50 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-diethylamino-propyl)benzamide (15.6 g, 100%).

$^1$H NMR (300 MHz, CDCl$_3$) δ 9.15 (br s, 1H), 7.91 (s, 1H), 7.75 (d, J=7.9 Hz, 1H), 7.58 (d, J=7.9 Hz, 1H), 7.29 (t, J=7.9 Hz, 1H), 3.56 (dd, J=10.3, 5.8 Hz, 2H), 2.67-2.53 (m, 6H), 1.74 (quint, J=5.7 Hz, 2H), 1.04 (t, J=7.1 Hz, 6H).

According to route (A), a reaction mixture of 3-bromo-N-(3-diethylamino-propyl)benzamide (156 mg, 0.5 mmole, 1 eq.), 3-amino-N-(pyrimidin-4-yl)benzamide (118 mg, 0.55 mmole, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-methyl-3-((3-((3-(4-methylpiperazin-1-yl)propyl)carbamoyl)phenyl)amino)-N-(pyridin-4-yl)benzamide (25) (16 mg, 7%).

Example 8: Compound (31) in Table I

According to route (E), a reaction mixture of 4-aminopyrimidine (1.0 g, 10.5 mmoles, 1 eq.), 3-nitrobenzoic acid (1.76 g, 10.5 mmoles, 1 eq.), EDCI.HCl (3.0 g, 15.8 mmoles, 1.5 eq.), triethylamine (1.6 mL, 11.6 mmoles, 1.1 eq.) and dimethylaminopyridine (129 mg, 1.05 mmole, 0.1 eq.) in dichloromethane (12 mL) was stirred at room temperature for 18 hours under an inert atmosphere of argon. The resulting precipitate was filtered and washed with water and dichloromethane. The organic filtrate was concentrated under reduced pressure and the resulting residue was purified by column chromatography on silica gel. The former precipitate and the purified compound were gathered to afford 3-nitro-N-(pyrimidin-4-yl)benzamide (2.5 g, 97%).

$^1$H NMR (300 MHz, d$_6$-DMSO) δ 11.69 (s, 1H), 9.00 (s, 1H), 8.83 (t, J=2.0 Hz, 1H), 8.77 (d, J=5.7 Hz, 1H), 8.51-8.41 (m, 2H), 8.22 (dd, J=5.7, 1.1 Hz, 1H), 7.84 (t, J=8.0 Hz, 1H).

According to route (C), 3-nitro-N-(pyrimidin-4-yl)benzamide (3.3 g, 13.5 mmoles, 1 eq.) and 10% Pd/C (719 mg) were placed in EtOH (50 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyrimidin-4-yl)benzamide (1.6 g, 55%).

$^1$H NMR (300 MHz, d$_6$-DMSO) δ 10.94 (s, 1H), 8.92 (dd, J=1.3, 0.5 Hz, 1H), 8.69 (dd, J=5.8, 0.5 Hz, 1H), 8.18 (dd, J=5.8, 1.3 Hz, 1H), 7.20-7.10 (m, 3H), 6.78 (dt, J=4.1, 2.3 Hz, 1H), 5.35 (s, 2H).

3-(4-methylpiperazin-1-yl)propylamine (1.9 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(4-methylpiperazin-1-yl-propyl)benzamide (2.7 g, 80%).

¹H NMR (300 MHz, CDCl₃) δ 8.61 (br s, 1H), 7.92 (s, 1H), 7.82 (d, J=7.9 Hz, 1H), 7.62 (d, J=7.9 Hz, 1H), 7.32 (t, J=7.9 Hz, 1H), 3.57 (q, J=5.2 Hz, 2H), 2.79-2.35 (m, 10H), 2.33 (s, 3H), 1.78 (quint, J=5.2 Hz, 2H).

According to route (A), a reaction mixture of 3-bromo-N-(4-methylpiperazin-1-yl-propyl)benzamide (576 mg, 1.7 mmole, 1 eq.), 3-amino-N-(pyrimidin-4-yl)benzamide (400 mg, 1.87 mmole, 1.1 eq.), Pd₂(dba)₃ (78 mg, 0.085 mmole, 5 mol %), XPhos (81 mg, 0.17 mmole, 10 mol %) and K₂CO₃ (940 mg, 6.8 mmoles, 4 eq.) in t-BuOH (7 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO₄, filtered and concentrated under reduced pressure. The resulting residue was purified by column chromatography on silica gel to give N-(3-(4-methylpiperazin-1-yl)propyl)-3-((3-(pyrimidin-4-ylcarbamoyl)phenyl)amino)benzamide (31) (54 mg, 7%).

Example 9: Compound (35) in Table I

According to route (B), 4-aminopyridine (2.1 g, 22 mmoles, 1.1 eq.) was placed in a 3N NaOH aqueous solution (28 mL) and dichloromethane (12 mL) was added to the solution. The reaction mixture was cooled down to 0° C. with an ice bath and a solution of 3-nitrobenzoyl chloride (3.7 g, 20 mmoles, 1 eq.) in dichloromethane (20 mL) was added dropwise. The reaction mixture was then stirred at room temperature for 18 hours under an inert atmosphere of argon. The resulting precipitate was filtered and washed with water and dichloromethane to afford 3-nitro-N-(pyridin-4-yl)benzamide (2.4 g, 50%).

¹H NMR (300 MHz, d₆-DMSO) δ 10.98 (s, 1H), 8.80 (s, 1H), 8.51 (d, J=6.2 Hz, 2H), 8.47 (d, J=7.9 Hz, 1H), 8.42 (d, J=7.9 Hz, 1H), 7.86 (t, J=7.9 Hz, 1H), 7.80 (d, J=6.2 Hz, 2H).

According to route (C), 3-nitro-N-(pyridin-4-yl)benzamide (1 g, 4.1 mmoles, 1 eq.) and 10% Pd/C (150 mg) were placed in EtOH (30 mL). The reaction mixture was stirred at room temperature for 16 hours under an atmosphere of H₂. The reaction mixture was then filtered on celite, washed with EtOH and the filtrate was concentrated under reduced pressure to afford 3-amino-N-(pyridin-4-yl)benzamide (660 mg, 75%).

¹H NMR (300 MHz, d₆-DMSO) δ 10.46 (s, 1H), 8.45 (dd, J=5.0, 1.3 Hz, 2H), 7.77 (dd, J=5.0, 1.3 Hz, 2H), 7.17 (t, J=7.9 Hz, 1H), 7.12-7.03 (m, 2H), 6.77 (dd, J=7.9, 1.2 Hz, 1H), 5.38 (s, 2H).

6-chloro-pyridine-2-carboxylic acid (4.4 g, 27.9 mmoles, 1 eq.) was placed under an inert atmosphere of argon. Thionyl chloride (8.1 mL, 111.6 mmoles, 4 eq.) was slowly added. The reaction mixture was heated at reflux and stirred for 48 hours. Upon cooling to room temperature, the reaction mixture was concentrated under reduced pressure. N,N-Diethylpropylenediamine (2.5 mL, 15.7 mmoles, 1.1 eq.) was placed in a 3N NaOH aqueous solution (20 mL) and dichloromethane (10 mL) was added to the solution. The reaction mixture was cooled down to 0° C. with an ice bath and a solution of the 6-chloro-pyridine-2-carbonyl chloride residue (2.5 g, 14.3 mmoles, 1 eq.) in dichloromethane (13 mL) was added dropwise. The reaction mixture was then stirred at room temperature for 18 hours under an inert atmosphere of argon. Upon decantation, the organic phase was washed with water, dried over MgSO₄, filtered and concentrated under reduced pressure to afford 6-chloro-pyridine-2-carboxylic acid (3-diethylamino-propyl)amide (2.7 g, 70%).

¹H NMR (300 MHz, CDCl₃) δ 9.22 (s, 1H), 8.10 (d, J=7.9 Hz, 1H), 7.77 (t, J=7.9 Hz, 1H), 7.40 (d, J=7.9 Hz, 1H), 3.53 (dd, J=12.1, 5.8 Hz, 2H), 2.65-2.49 (m, 6H), 1.82-1.68 (m, 2H), 1.06 (t, J=7.1 Hz, 6H).

According to route (A), a reaction mixture of 6-chloro-pyridine-2-carboxylic acid (3-diethylamino-propyl)amide (135 mg, 0.5 mmole, 1 eq.), 3-amino-N-(pyridin-4-yl)benzamide (117 mg, 0.55 mmole, 1.1 eq.), Pd₂(dba)₃ (23 mg, 0.025 mmole, 5 mol %), XPhos (24 mg, 0.05 mmole, 10 mol %) and K₂CO₃ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO₄, filtered and concentrated under reduced pressure. The resulting residue was purified by column chromatography on silica gel to give N-(3-(diethylamino)propyl)-6-((3-(pyridin-4-ylcarbamoyl)phenyl)amino)picolinamide (35) (79 mg, 35%).

Example 10: Compound (39) in Table I

According to route (D), a reaction mixture of 4-(methylamino)pyridine (1.25 g, 11.6 mmoles, 1.0 eq.), 3-nitrobenzoyl chloride (2.57 g, 13.9 mmoles, 1.2 eq.), N,N-diisopropylethylamine (3.02 mL, 17.3 mmoles, 1.5 eq.) and dimethylaminopyridine (103 mg, 1.41 mmole, 1 eq.) in dichloromethane (25 mL) was stirred at room temperature for 18 hours under an inert atmosphere of argon. The organic phase was washed with water, dried over MgSO₄, filtered and concentrated under reduced pressure. The resulting residue was purified by column chromatography on silica gel to give N-methyl-3-nitro-N-(pyridin-4-yl)benzamide (2.96 g, 100%).

¹H NMR (300 MHz, CDCl₃) δ 8.50 (dd, J=4.6, 1.6 Hz, 2H), 8.25 (s, 1H), 8.21 (d, J=7.9 Hz, 1H), 7.62 (d, J=7.9 Hz, 1H), 7.45 (t, J=7.9 Hz, 1H), 6.98 (dd, J=4.6, 1.6 Hz, 2H), 3.56 (s, 3H).

According to route (C), N-methyl-3-nitro-N-(pyridin-4-yl)benzamide (2.96 g, 11.5 mmoles, 1 eq.) and 10% Pd/C (450 mg) were placed in EtOH (100 mL). The reaction mixture was stirred at room temperature for 16 hours under an atmosphere of H₂. The reaction mixture was then filtered on celite, washed with EtOH and the filtrate was concentrated under reduced pressure to afford 3-amino-N-methyl-N-(pyridin-4-yl)benzamide (2.5 g, 96%).

¹H NMR (300 MHz, d₆-DMSO) δ 8.40 (dd, J=4.6, 1.6 Hz, 2H), 7.14 (dd, J=4.6, 1.6 Hz, 2H), 6.89 (t, J=7.9 Hz, 1H), 6.59 (s, 1H), 6.53 (d, J=7.9 Hz, 1H), 6.34 (d, J=7.9 Hz, 1H), 5.22 (s, 2H), 3.37 (s, 3H).

2-chloro-isonicotinic acid (2.0 g, 12.7 mmoles, 1 eq.) placed in acetonitrile (25.4 mL) under an inert atmosphere of argon. Thionyl chloride (1.2 mL, 16.5 mmoles, 1.3 eq.) and DMF (100 μL, 1.27 mmole, 0.1 eq.) were slowly added. The reaction mixture was heated at reflux and stirred for 1 hour. Upon cooling to room temperature, the reaction mixture was concentrated under reduced pressure. 3-(4-methylpiperazin-1-yl)propylamine (2.7 mL, 15.7 mmoles, 1.2 eq.) was placed in a 3N NaOH aqueous solution (20 mL) and dichloromethane (10 mL) was added to the solution. The reaction mixture was cooled down to 0° C. with an ice bath and a solution of the 2-chloro-isonicotinoyl chloride residue (12.7 mmoles, 1 eq.) in dichloromethane (13 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 2-chloro-N-[3-(4-methyl-piperazin-1-yl)-propyl]-isonicotinamide (1.8 g, 43%).

$^1$H NMR (300 MHz, CDCl$_3$) δ 9.03 (s, 1H), 8.51 (d, J=4.9 Hz, 1H), 7.71-7.64 (m, 2H), 3.58 (dd, J=10.8, 5.0 Hz, 2H), 2.66-2.40 (m, 10H), 2.32 (s, 3H), 1.84-1.73 (m, 2H).

According to route (A), a reaction mixture of 2-chloro-N-[3-(4-methyl-piperazin-1-yl)-propyl]-isonicotinamide (148 mg, 0.5 mmole, 1 eq.), 3-amino-N-methyl-N-(pyridin-4-yl)benzamide (125 mg, 0.55 mmole, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give 2-((3-(methyl(pyridin-4-yl)carbamoyl)phenyl)amino)-N-(3-(4-methylpiperazin-1-yl)propyl)iso nicotinamide (39) (43 mg, 18%).

Example 11: Compound (41) in Table I

According to route (E), a reaction mixture of 4-aminopyrimidine (885 mg, 9.3 mmoles, 1.1 eq.), 3-nitrobenzoic acid (1.4 g, 8.4 mmoles, 1 eq.), EDCI.HCl (2.4 g, 12.6 mmoles, 1.5 eq.), triethylamine (1.3 mL, 9.3 mmoles, 1.1 eq.) and dimethylaminopyridine (103 mg, 0.8 mmole, 0.1 eq.) in dichloromethane (10 mL) was stirred at room temperature for 18 hours under an inert atmosphere of argon. The resulting precipitate was filtered and washed with water and dichloromethane. The organic filtrate was concentrated under reduced pressure and the resulting residue was purified by column chromatography on silica gel. The former precipitate and the purified compound were gathered to afford 3-nitro-N-(pyrimidin-4-yl)benzamide (1.35 g, 66%).

$^1$H NMR (300 MHz, d$_6$-DMSO) δ 11.69 (s, 1H), 8.99 (s, 1H), 8.83 (s, 1H), 8.76 (d, J=5.6 Hz, 1H), 8.50-8.40 (m, 2H), 8.22 (dt, J=5.6, 1.2 Hz, 1H), 7.83 (t, J=7.9 Hz, 1H).

According to route (C), 3-nitro-N-(pyrimidin-4-yl)benzamide (1.35 g, 5.5 mmoles, 1 eq.) and 10% Pd/C (303 mg) were placed in EtOH (30 mL). The reaction mixture was stirred at room temperature for 16 hours under an atmosphere of H$_2$. The reaction mixture was then filtered on celite, washed with EtOH and the filtrate was concentrated under reduced pressure to afford 3-amino-N-(pyrimidin-4-yl)benzamide (1.2 g, 100%).

$^1$H NMR (300 MHz, d$_6$-DMSO) δ 10.93 (br s, 1H), 8.92 (dd, J=1.3, 0.5 Hz, 1H), 8.69 (dd, J=5.8, 0.5 Hz, 1H), 8.18 (dd, J=5.8, 1.3 Hz, 1H), 7.20-7.12 (m, 3H), 6.78 (dt, J=4.1, 2.3 Hz, 1H), 5.35 (s, 2H).

2-chloro-isonicotinic acid (2.0 g, 12.7 mmoles, 1 eq.) was placed in acetonitrile (25.4 mL) under an inert atmosphere of argon. Thionyl chloride (1.2 mL, 16.5 mmoles, 1.3 eq.) and DMF (100 μL, 1.27 mmole, 0.1 eq.) were slowly added. The reaction mixture was heated at reflux and stirred for 1 hour. Upon cooling to room temperature, the reaction mixture was concentrated under reduced pressure. N,N-Diethylpropylenediamine (2.5 mL, 15.7 mmoles, 1.2 eq.) was placed in a 3N NaOH aqueous solution (20 mL) and dichloromethane (10 mL) was added to the solution. The reaction mixture was cooled down to 0° C. with an ice bath and a solution of the 2-chloro-isonicotinoyl chloride residue (12.7 mmoles, 1 eq.) in dichloromethane (13 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 2-chloro-N-(3-diethylamino-propyl)isonicotinamide (1.8 g, 47%).

$^1$H NMR (300 MHz, CDCl$_3$) δ 9.62 (s, 1H), 8.49 (d, J=5.0 Hz, 1H), 7.66 (s, 1H), 7.58 (d, J=5.1 Hz, 1H), 3.59 (dd, J=10.4, 5.0 Hz, 2H), 2.70-2.55 (m, 6H), 1.81-1.72 (m, 2H), 1.06 (t, J=7.1 Hz, 6H).

According to route (A), a reaction mixture of 2-chloro-N-(3-diethylamino-propyl)isonicotinamide (135 mg, 0.5 mmole, 1 eq.), 3-amino-N-(pyrimidin-4-yl)benzamide (118 mg, 0.55 mmole, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-(3-(diethylamino)propyl)-2-((3-(pyrimidin-4-ylcarbamoyl)phenyl)amino)isonicotinamide (41) (79 mg, 35%).

Example 12: Compound (44) in Table I

According to route (E), a reaction mixture of 4-aminopyridine (837 mg, 8.9 mmoles, 1.3 eq.), 2-nitro-isonicotinic acid (1.15 g, 6.8 mmoles, 1 eq.), EDCI.HCl (1.7 g, 8.9 mmoles, 1.3 eq.), N,N-diisopropylethylamine (3.0 mL, 17.1 mmoles, 2.5 eq.) and dimethylaminopyridine (272 mg, 2.2 mmoles, 0.25 eq.) in dichloromethane (7 mL) was stirred at room temperature for 18 hours under an inert atmosphere of argon. The organic phase was washed with water, dried over MgSO$_4$, filtered and concentrated under reduced pressure. The resulting residue was purified by column chromatography on silica gel to give 2-nitro-N-pyridin-4-yl-isonicotinamide (835 mg, 50%).

$^1$H NMR (300 MHz, MeOD) δ 8.86-8.80 (m, 2H), 8.50 (dd, J=5.0, 1.6 Hz, 2H), 8.31 (dd, J=4.8, 1.5 Hz, 1H), 7.88 (dd, J=5.0, 1.6 Hz, 2H).

According to route (C), 2-nitro-N-pyridin-4-yl-isonicotinamide (835 mg, 3.4 mmoles, 1 eq.) and 10% Pd/C (150 mg) were placed in EtOH (50 mL). The reaction mixture was stirred at room temperature for 16 hours under an atmosphere of H$_2$. The reaction mixture was then filtered on celite, washed with EtOH and the filtrate was concentrated under reduced pressure to afford 2-amino-N-pyridin-4-yl-isonicotinamide (727 mg, 99%).

$^1$H NMR (300 MHz, d$_6$-DMSO) δ 10.61 (s, 1H), 8.48 (dd, J=4.8, 1.5 Hz, 2H), 8.07 (d, J=5.3 Hz, 1H), 7.75 (dd, J=4.8, 1.5 Hz, 2H), 6.91 (d, J=5.3 Hz, 1H), 6.86 (s, 1H), 6.28 (s, 2H).

2-chloro-isonicotinic acid (2.0 g, 12.7 mmoles, 1 eq.) was placed in acetonitrile (25.4 mL) under an inert atmosphere of argon. Thionyl chloride (1.2 mL, 16.5 mmoles, 1.3 eq.) and DMF (100 μL, 1.27 mmole, 0.1 eq.) were slowly added. The reaction mixture was heated at reflux and stirred for 1 hour. Upon cooling to room temperature, the reaction mixture was concentrated under reduced pressure. N,N-Diethylpropylenediamine (2.5 mL, 15.7 mmoles, 1.2 eq.) was placed in a 3N NaOH aqueous solution (20 mL) and dichloromethane (10 mL) was added to the solution. The reaction mixture was cooled down to 0° C. with an ice bath and a solution of the 2-chloro-isonicotinoyl chloride residue (12.7 mmoles, 1 eq.) in dichloromethane (13 mL) was added dropwise. The reaction mixture was then stirred at room temperature for 18 hours under an inert atmosphere of argon. Upon decantation, the organic phase was washed with water, dried over $MgSO_4$, filtered and concentrated under reduced pressure to afford 2-chloro-N-(3-diethylamino-propyl)isonicotinamide (1.8 g, 47%).

$^1$H NMR (300 MHz, $CDCl_3$) δ 9.62 (s, 1H), 8.49 (d, J=5.0 Hz, 1H), 7.66 (s, 1H), 7.58 (d, J=5.1 Hz, 1H), 3.59 (dd, J=10.4, 5.0 Hz, 2H), 2.70-2.55 (m, 6H), 1.81-1.72 (m, 2H), 1.06 (t, J=7.1 Hz, 6H).

According to route (A), a reaction mixture of 2-chloro-N-(3-diethylamino-propyl)isonicotinamide (135 mg, 0.5 mmole, 1 eq.), 2-amino-N-pyridin-4-yl-isonicotinamide (118 mg, 0.55 mmole, 1.1 eq.), $Pd_2(dba)_3$ (23 mg, 0.025 mmole, 5 mol %), XPhos (24 mg, 0.05 mmole, 10 mol %) and $K_2CO_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give N-(3-(diethylamino)propyl)-2-((4-(pyridin-4-ylcarbamoyl)pyridin-2-yl)amino)isonicotinamide (44) (70 mg, 31%).

Example 13: Compound (47) in Table I

According to route (E), a reaction mixture of 4-aminopyridine (837 mg, 8.9 mmoles, 1.3 eq.), 2-nitro-isonicotinic acid (1.15 g, 6.8 mmoles, 1 eq.), EDCI.HCl (1.7 g, 8.9 mmoles, 1.3 eq.), N,N-diisopropylethylamine (3.0 mL, 17.1 mmoles, 2.5 eq.) and dimethylaminopyridine (272 mg, 2.2 mmoles, 0.25 eq.) in dichloromethane (7 mL) was stirred at room temperature for 18 hours under an inert atmosphere of argon. The organic phase was washed with water, dried over $MgSO_4$, filtered and concentrated under reduced pressure. The resulting residue was purified by column chromatography on silica gel to give 2-nitro-N-pyridin-4-yl-isonicotinamide (835 mg, 50%).

$^1$H NMR (300 MHz, MeOD) δ 8.86-8.80 (m, 2H), 8.50 (dd, J=5.0, 1.6 Hz, 2H), 8.31 (dd, J=4.8, 1.5 Hz, 1H), 7.88 (dd, J=5.0, 1.6 Hz, 2H).

According to route (C), 2-nitro-N-pyridin-4-yl-isonicotinamide (835 mg, 3.4 mmoles, 1 eq.) and 10% Pd/C (150 mg) were placed in EtOH (50 mL). The reaction mixture was stirred at room temperature for 16 hours under an atmosphere of $H_2$. The reaction mixture was then filtered on celite, washed with EtOH and the filtrate was concentrated under reduced pressure to afford 2-amino-N-pyridin-4-yl-isonicotinamide (727 mg, 99%).

$^1$H NMR (300 MHz, $d_6$-DMSO) δ 10.61 (s, 1H), 8.48 (dd, J=4.8, 1.5 Hz, 2H), 8.07 (d, J=5.3 Hz, 1H), 7.75 (dd, J=4.8, 1.5 Hz, 2H), 6.91 (d, J=5.3 Hz, 1H), 6.86 (s, 1H), 6.28 (s, 2H).

N,N-diethylpropylenediamine (8.7 mL, 55 mmoles, 1.1 eq.) was placed in a 3N NaOH aqueous solution (71 mL) and dichloromethane (30 mL) was added to the solution. The reaction mixture was cooled down to 0° C. with an ice bath and a solution of 3-bromobenzoyl chloride (6.6 mL, 50 mmoles, 1 eq.) in dichloromethane (50 mL) was added dropwise. The reaction mixture was then stirred at room temperature for 18 hours under an inert atmosphere of argon. Upon decantation, the organic phase was washed with water, dried over $MgSO_4$, filtered and concentrated under reduced pressure to afford 3-bromo-N-(3-diethylamino-propyl)benzamide (14.6 g, 94%).

$^1$H NMR (300 MHz, $CDCl_3$) δ 9.16 (br s, 1H), 7.91 (t, J=1.8 Hz, 1H), 7.75 (d, J=7.9 Hz, 1H), 7.58 (d, J=7.9 Hz, 1H), 7.29 (t, J=7.9 Hz, 1H), 3.56 (dd, J=10.1, 5.7 Hz, 2H), 2.72-2.50 (m, 6H), 1.75 (quint, J=5.7 Hz, 2H), 1.05 (t, J=7.1 Hz, 6H)

According to route (A), a reaction mixture of 3-bromo-N-(3-diethylamino-propyl)benzamide (156 mg, 0.5 mmole, 1 eq.), 2-amino-N-pyridin-4-yl-isonicotinamide (118 mg, 0.55 mmole, 1.1 eq.), $Pd_2(dba)_3$ (23 mg, 0.025 mmole, 5 mol %), XPhos (24 mg, 0.05 mmole, 10 mol %) and $K_2CO_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give 2-((3-((3-(diethylamino)propyl)carbamoyl)phenyl)amino)-N-(pyridin-4-yl)isonicotinamide (47) (52 mg, 23%).

Example 14: Compound (51) in Table I

According to route (E), a reaction mixture of 4-aminopyridine (1.57 g, 16.7 mmoles, 1.3 eq.), 2-nitro-isonicotinic acid (2.16 g, 12.9 mmoles, 1 eq.), EDCI.HCl (3.69 g, 19.3 mmoles, 1.5 eq.), N,N-diisopropylethylamine (5.3 mL, 32.1 mmoles, 2.5 eq.) and dimethylaminopyridine (392 mg, 3.2 mmoles, 0.25 eq.) in dichloromethane (15 mL) was stirred at room temperature for 18 hours under an inert atmosphere of argon. The organic phase was washed with water, dried over $MgSO_4$, filtered and concentrated under reduced pressure. The resulting residue was purified by column chromatography on silica gel to give 2-nitro-N-pyridin-4-yl-isonicotinamide (1.68 g, 54%).

$^1$H NMR (300 MHz, MeOD) δ 8.86-8.80 (m, 2H), 8.50 (dd, J=5.0, 1.6 Hz, 2H), 8.31 (dd, J=4.8, 1.5 Hz, 1H), 7.88 (dd, J=5.0, 1.6 Hz, 2H).

According to route (C), 2-nitro-N-pyridin-4-yl-isonicotinamide (1.1 g, 4.5 mmoles, 1 eq.) and 10% Pd/C (240 mg) were placed in EtOH (50 mL). The reaction mixture was stirred at room temperature for 16 hours under an atmosphere of $H_2$. The reaction mixture was then filtered on celite, washed with EtOH and the filtrate was concentrated under reduced pressure to afford 2-amino-N-pyridin-4-yl-isonicotinamide (898 mg, 93%).

$^1$H NMR (300 MHz, $d_6$-DMSO) δ 10.68 (s, 1H), 8.48 (d, J=5.9 Hz, 2H), 8.07 (d, J=5.2 Hz, 1H), 7.77 (d, J=5.9 Hz, 2H), 6.93 (d, J=5.2 Hz, 1H), 6.87 (s, 1H), 6.27 (s, 2H).

3-(4-methylpiperazin-1-yl)propylamine (1.9 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 18 hours under an inert atmosphere of argon. Upon decantation, the organic phase was washed with water, dried over $MgSO_4$, filtered and concentrated under reduced pressure to afford 3-bromo-N-(4-methylpiperazin-1-yl-propyl)benzamide (2.7 g, 80%).

$^1$H NMR (300 MHz, $CDCl_3$) δ 8.61 (br s, 1H), 7.92 (s, 1H), 7.82 (d, J=7.9 Hz, 1H), 7.62 (d, J=7.9 Hz, 1H), 7.32 (t,

J=7.9 Hz, 1H), 3.57 (q, J=5.2 Hz, 2H), 2.79-2.35 (m, 10H), 2.33 (s, 3H), 1.78 (quint, J=5.2 Hz, 2H).

According to route (A), a reaction mixture of 3-bromo-N-(4-methylpiperazin-1-yl-propyl)benzamide (123 mg, 0.36 mmole, 1 eq.), 2-amino-N-pyridin-4-yl-isonicotinamide (96 mg, 0.45 mmole, 1.1 eq.), $Pd_2(dba)_3$ (17 mg, 0.018 mmole, 5 mol %), XPhos (17 mg, 0.036 mmole, 10 mol %) and $K_2CO_3$ (200 mg, 1.44 mmole, 4 eq.) in t-BuOH (1.4 mL) was heated at 90° C. and stirred for 48 hours under an inert atmosphere of argon. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give 2-((3-((3-(4-methylpiperazin-1-yl)propyl)carbamoyl)phenyl)amino)-N-(pyridin-4-yl)isonicotinamide (51) (34 mg, 20%).

Example 15: Pharmacological Data

Standard Operating Procedure:
Effect of Drug Compounds on Invasion of MDA-MB231-D3H2LN Cells into Collagen
Background:
A key step in the generation of tumor metastasis is the invasion of tumor cells into the extracellular matrix, a major component of which is collagen. Therefore, the invasion of tumor cells into collagen in vitro may be indicative of the generation of metastasis in vivo. E. g., MDA-MB231-luc-D3H2LN mouse breast cancer cells display indeed both higher invasion into collagen in vitro and a higher metastatic potential in vivo as compared to MDA-MB231 cells (from which they were derived). Using these MDA-MB231-luc-D3H2LN cells as a model, the aim of the experiment described here is to identify drug compounds that inhibit the invasion of tumor cells into collagen in vitro, therefore potentially inhibiting also the generation of tumor metastasis in vivo.
Assay Principle:
Step 1:
Preparation of cells at the bottom of a collagen gel: Cells are suspended in a liquid collagen solution (4° C.), distributed into BSA-coated wells, and then collected at the bottom of the wells by centrifugation. The collagen is then solidified by incubation at 37° C. The BSA coating improves the adhesion of the collagen gel.
Step 2:
Pre-treatment with the compounds to be tested: Concentrated drug solutions are then added on top of the collagen, and cells are pre-incubated for 48 h with the drugs at low serum conditions (0.025% FBS).
Step 3:
Stimulation of invasion: Medium with 5% FBS is then added in order to stimulate invasion of the cells into the collagen gel.
Step 4:
Viability assay, fixation and staining: Following another 24 h incubation, an MTS assay is performed directly on the cells in the collagen. Then, cells are fixed and nuclei are stained.
Step 5:
Analysis: Finally, plates are analyzed using an automated microscope. Fluorescent beads that have been included into the BSA coating serve to detect the bottom of the wells. Pictures of the stained nuclei are taken at the same level (0 µm) as well as 25 µm and 50 µm above.

Note:
In order to detect possible toxic effects, all compounds are tested in parallel in a viability assay. The viability assay is performed in parallel on serum-starved cells (as in the invasion assay) vs. cells under normal culture conditions (10% FBS).
Materials:
General Equipment:
Freezer (−20° C.), refrigerator (4° C.), ice machine, water bath (37° C.), incubator (37° C./5% $CO_2$), cell culture hood, vortex, vacuum pump, microscope, Pipet aid, micropipettes (for pipetting 1-1000 µl), multichannel pipettes (for pipetting 20-200 µl), standard cell culture centrifuge, refrigerated centrifuge for 96 well plates.
General Consumables:
Sterile tubes (1.5/15/50 ml), sterile pipettes (5/10/25 ml), sterile micropipette tips (for pipetting 1-1000 µl), sterile Pasteur pipettes, sterile reagent reservoirs.
General Products:
Sterile PBS, sterile Milli-Q water, DMSO, decomplemented FBS (frozen aliquots), 0.1 N NaOH, 1 M Hepes, MEM without serum (not older than 1 month), 2.5×MEM without serum (not older than 1 month), MEM with 10% FBS (not older than one month), 0.25% trypsin/1 mM EDTA solution, 37% formaldehyde solution.
Specific Equipment:
plate reader: Tecan Infinite F200
automated microscope: Cellomics ArrayScan $V^{TT}$ HCS Reader
Specific Consumables:
sterile black 96 well plates (for the invasion assay): Perkin Elmer ViewPlate-96 F TC, ref. 6005225
Specific Products:
rat tail collagen, type 1: BD Biosciences, ref. 354236 (note: each new lot has to be validated)
red fluorescent beads (1 µm diameter): Invitrogen, ref. F13083
Y-27632 (5 mM aqueous solution): Calbiochem, ref. 688001 (in solution) or 688000 (dry powder)
BSA without fatty acids (sterile-filtered 4% aqueous solution): Sigma, ref. A8806 (dry powder)
Hoechst 33342 nuclear stain (10 mg/ml): Invitrogen, ref. H3570
MTS reagent: Promega CellTiter CellTiter 96® AQueous One Solution Reagent, ref. G3581
drug compounds to be tested: generally 50 mM in 100% DMSO (aliquots stored at −20° C., then at 4° C. for max. 3 months)
MDA-MB231-luc-D3H2LN Cells:
Limits for the Cell Cultures to be Used in the Assays:
total passage number: max. 30
last passage: between 2 and 4 days before, between 1:3 and 1:20
cell density: between 50 and 90% (optimally 70%) (between 1 and $2 \times 10^6$ cells per 100 mm dish)

Experimental Procedures

General Considerations:
Controls and Plate Maps:
Negative control: No drug (just DMSO at equivalent concentration). Positive control: 10 µM Y-27632. To avoid edge effects, cells are added only to the 60 central wells B2-G11; lines A and H receive only collagen without cells (blank for the MTS assay) columns 1 and 12 remain free. Each drug is tested at least in triplicate. The positive and negative controls should be tested in several triplicates at different positions on each plate. Typical plate map (−=negative control, +=positive control, 1-12=12 different test conditions, i. e. different drug compounds or concentrations):

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | − | 1 | 2 | 3 | + | − | 4 | 5 | 6  | +  |    |
| C |   | − | 1 | 2 | 3 | + | − | 4 | 5 | 6  | +  |    |
| D |   | − | 1 | 2 | 3 | + | − | 4 | 5 | 6  | +  |    |
| E |   | + | 7 | 8 | 9 | − | + | 10 | 11 | 12 | −  |    |
| F |   | + | 7 | 8 | 9 | − | + | 10 | 11 | 12 | −  |    |
| G |   | + | 7 | 8 | 9 | − | + | 10 | 11 | 12 | −  |    |
| H |   |   |   |   |   |   |   |   |   |    |    |    |

The volumes or other quantities indicated in the following are required for four 96 well plates according to the plate map above. According to the number of tested compounds, the volumes and other quantities should be adapted.

Day 1: Preparation and Treatment of the Cells (all Steps are Performed Under a Cell Culture Hood):

Preparation of 4× concentrated drug solutions in MEM+ 0.1% FBS+2% Lutrol E-400+0.8% DMSO: Mix each 620 µl MEM+0.1% FBS+2% Lutrol E-400 with each 4 µl DMSO+ each 1 µl of the 50 mM compound stock solutions (yielding 20 µM compound and 0.8% DMSO). If the desired final compound concentration is <5 µM, then further dilute in MEM+0.1% FBS+0.8% DMSO. Negative control: MEM+ 0.1% FBS+2% Lutrol E-400+0.8% DMSO without any drug. Preparation of the positive control: Mix 4.5 ml MEM+ 0.1% FBS+2% Lutrol E-400+0.8% FBS with 36 µl 5 mM Y-27632 (freshly thawed aliquot) (yielding 40 µM).

Coating of the Plates for the Invasion Assay:

mix 38 ml MEM without serum+2 ml 4% BSA without fatty acids+4 µl vortexed fluorescent beads (i. e. dilute 1:10000), vortex, distribute 100 µl/well into the plate for the invasion assay centrifuge 30' with 1800×g at 4° C. (e. g. 3000 rpm in a Jouan GR412 centrifuge)

remove supernatants by aspiration

Preparation of a 10×10$^6$ Cells/Ml Cell Suspension (During the Centrifugation of the Plates):

remove medium, wash cells with ~10 ml/dish PBS, add 1 ml/dish 0.25% trypsin/1 mM EDTA incubate 30-60 s at 37° C.

add 5-10 ml/dish pre-warmed MEM+10% FBS homogenize by pipetting up and down using a 10 ml pipette, pool all count cells centrifuge 3×10$^6$ (or more) cells for 5' with 150×g at RT (850 rpm in a std. cell culture centrifuge)

remove supernatant, resuspend cell pellet in 0.3 ml (or more, respectively) MEM without serum, yielding 10×10$^6$ cells/ml Preparation of the Invasion Assay (on Ice; Start During the Centrifugation of the Cells):

mix on ice in a pre-chilled tube: example for a 4.01 mg/ml collagen stock solution; volumes of collagen and water to be adapted according to the stock concentration of each collagen lot:

16 ml 2.5×MEM
5.452 ml water
0.8 ml 1 M Hepes
0.39 ml 1 N NaOH
16.958 ml 4.01 mg/ml collagen stock solution homogenize by pipetting gently up and down (keep on ice).

To 29.7 ml of this, add 300 µl of the 10×10$^6$ cells/ml cell suspension, homogenize by pipetting gently up and down (yields 0.1×10$^6$ cells/ml in 1.7 mg/ml collagen in 30 ml 1×MEM+20 µM Hepes) (keep on ice). To the remaining 9.9 ml, add 100 µl MEM without serum, homogenize by pipetting gently up and down (yields 1.7 mg/ml collagen in 10 ml 1×MEM+20 µM Hepes without cells) (keep on ice).

distribute 100 µl/well into the coated wells (all on ice), according to the plate map above (lines A and H: collagen without cells, lines B-G: collagen with cells: 10000 cells/ well)

centrifuge 5' with 200×g at 4° C. (e. g. 1000 rpm in a Jouan GR412 centrifuge)

add 200 µl/well PBS to all free wells (columns 1 and 12)

incubate 30' at 37° C./5% $CO_2$ (solidification of the collagen)

Treatment with the Drugs:

add each 33 µl/well of the 4× concentrated drug solutions in MEM+0.1% FBS+2% Lutrol E-400+0.8% DMSO to the corresponding wells (yields 1× concentrated drugs in MEM+0.025% FBS+0.5% Lutrol E-400+0.2% DMSO final)

incubate 48 h at 37° C./5% $CO_2$

Day 3: Addition of FBS to Stimulate the Invasion:

prepare MEM+5% FBS: 19 ml MEM without serum+1 ml FBS (freshly thawed aliquot)

add 33 µl/well to all wells incubate 24 h at 37° C./5% $CO_2$

Day 4: Viability Assay, Fixation and Staining:

Viability Assay: MTS Assay:

add each 33 µl/well of the MTS reagent, incubate 3-4 h at 37° C./5% $CO_2$ read absorbance at 490 nm (proportional to the viability)

calculate the background-corrected signals by subtracting the means of the background signals in absence of cells from the corresponding signals in presence of cells normalize the background-corrected signals with respect to the mean signal of the negative controls (no drug) (viabilities are thus expressed in "% of control")

Fixation and Staining (Formaldehyde Must be Manipulated Under a Fume Cupboard):

freshly prepare 1 µg/ml Hoechst 33342 in 18.5% formaldehyde: 10 ml PBS (not necessarily sterile)+10 ml 37% formaldehyde+2 µl 10 mg/ml Hoechst 33342 add 50 µl/well to all wells with cells (yields 3.7% formaldehyde final) seal with black film (provided with the plates)

incubate at least 7 h at RT

Day 5 (Typically): (Min. 7 h/Max. 2 Weeks after Fixation and Staining): Analysis of the Invasion Assay:

Lecture using the Cellomics ArrayScan V$^{TI}$ HCS Reader:

BioApplication: SpotDetector.V3

Plate type: Perkin Elmer 96 well

Parameters of the Assay Protocol:

objective: 10× (NA 0.45)

apotome: yes (resulting optical slice: 11.7 µM)

fields per well: 6-8 autofocus in each field autofocus channel: 1 channel 1 (autofocus on, and photo of the fluorescent beads at the bottom of the wells): filter: XF93-TRITC; exposure time: usually between 0.002 and 0.01 s channel 2 (photo of the stained cells at the same level as the fluorescent beads): filter: XF93-Hoechst; exposure time: usually between 0.02 and 0.1 s; z offset: 0 µM channel 3 (photo of the stained cells 25 µM above the fluorescent beads): filter: XF93-Hoechst; exposure time: usually between 0.02 and 0.1 s; z offset: −25 µM channel 4 (photo of the fluorescent cells 50 µM above the fluorescent beads): filter: XF93-Hoechst; exposure time: usually between 0.02 and 0.1 s; z offset: −50 µM object identification: method: fixed threshold: 100-32767

| object selection parameters: | min. | max. |
|---|---|---|
| SpotArea: | 20 | 1000000000000 |
| SpotShapeBFR: | 0.2 | 1000 |
| SpotShapeBAR: | 0 | 1000 |
| SpotAvgInten: | 200 | 32767 |
| SpotTotalInten: | ≤4000 (thus not limiting) | 1000000000000 |
| TargetAvgPnten: | 0 | 32767 |
| TargetTotalInten: | 0 | 1000000000000 |

Analysis of the Results of the Scan Using vHCS Viewer:
export the results: for each well:
number of valid fields
number of objects in each valid field in each of the channels 2, 3 and 4 ("field details")
mean numbers of objects per valid field for each well, in each of the channels 2, 3 and 4
exclude wells with less than 6 valid fields per well from further analysis
visually check all photos for any apparent problems, such as bad focusing or obviously inhomogeneous collagen structure ("bubbles", . . . ), . . . ; in case of apparent problems: document, then exclude the corresponding wells from further analysis Further Analysis of the Results of the Invasion Assay (Using e. g. Excel):
for each well, calculate the mean invasion distance of the counted cells: (25 µm×number of cells at 25 µm+50 µm×number cells at 50 µm)/sum of cells at 0, 25 and 50 µm
for all four parameters (number of cells at 0 µm, number of cells at 25 µm, number of cells at 50 µm, mean invasion distance of the counted cells), calculate means, SD and CV of the replicates
invalidate any replicate with a CV≥50% (compound to be re-tested, or assay to be repeated if CV≥50% for the untreated negative control or the compound Y-27632-treated positive control). Y27632 is a selective inhibitor of the Rho-associated protein kinase p160ROCK of the following formula

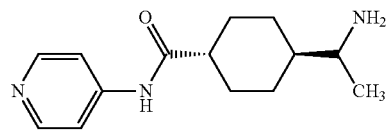 [SMILES: CC(N)[C@H]1CC[C@H](C(=O)Nc2ccncc2)CC1]

validate the assay only if the mean invasion distance of the cells treated with 10 µM Y-27632 (positive control) is decreased by ≥40% as compared to the untreated negative control Final analysis: Determine the concentration at which a given compound has 50% of the anti-invasive effect of the positive control (10 µM Y-27632). Determine the toxicity (=loss of viability) of the compound under these conditions.

Toxicity Assays (Under Normal Cell Culture Conditions):
Compounds were prepared as for the invasion assay, and then added to either MDA-MB231-luc-D3H2LN cells (2000/well) under normal culture conditions (MEM+10% FBS), or human PBMC (75000/well, in RPMI+10% FBS+IL-2) in standard 96-well tissue culture plates. After 72 h incubation, a standard MTS assay was performed according to the manufacturer's instructions (Promega Ref. G3581). Compounds were tested at various concentrations (concentration-response curves) in order to determine the concentrations at which 50% toxicity is obtained.

hERG Channel Inhibition:
Performed by Porsolt & Partners (Z. A. de Glatigné, 53940 Le Genest-Saint-Isle, France). Briefly, each 3 hERG-transfected HEK293 cells were superfused with the compounds at 1 and 10 µM, and the hERG channel current was measured by electrophysiology, as described by Crumb et al., J. Pharmacol. Exp. Ther. 2000.

Results
The table below indicates the toxicity on MDA-MB231, on PBMC, the anti-invasive effect, and the inhibition of hERG channel.

| | MDA tox: 50% tox. at (µM) | | | PBMC tox.: 50% tox. at (µM) | | | MDA: Inhib. of invasion: 0.5 × eff. of 10 µM Y-27632 at (µM) | | | (+ MDA tox. under these cond.) | % hERG inhibition in transfected HEK (n = 3) | | | |
|---|---|---|---|---|---|---|---|---|---|---|---|---|---|---|
| | | | | | | | | | | | at 1 µM | | at 10 µM | |
| N° | av | SD | n | av | SD | n | av | SD | n | % tox | av | SEM | av | SEM |
| 1 | 46 | 10 | 5 | 51 | 11 | 10 | 0.13 | 0.1 | 9 | <10 | 13 | 2 | 47 | 2 |
| 2 | 103 | 3 | 2 | 156 | 35 | 4 | >5 | — | 2 | | | | | |
| 3 | 51 | 0 | 2 | 51 | 10 | 4 | 0.29 | 0.1 | 4 | <10 | 14 | 4 | 54 | 4 |
| 4 | 54 | 2 | 2 | 42 | 11 | 4 | 0.21 | 0.1 | 4 | <10 | 6 | 0 | 59 | 2 |
| 5 | 68 | 3 | 2 | 74 | 19 | 4 | 1.31 | 0.5 | 3 | <10 | 1 | 2 | 29 | 3 |
| 6 | 58 | 7 | 2 | 100 | 31 | 4 | 0.16 | 0.0 | 3 | <10 | | | | |
| 7 | 25 | 13 | 2 | 38 | 8 | 4 | 0.11 | 0.0 | 2 | <10 | | | | |
| 8 | >>100 | — | 3 | | | | 7.50 | 2.5 | 2 | | | | | |
| 9 | 44 | 6 | 2 | 36 | 3 | 4 | 0.28 | 0.0 | 2 | <10 | 5 | 4 | 50 | 4 |
| 10 | 45 | 6 | 2 | 29 | 16 | 4 | 0.53 | 0.2 | 2 | <10 | | | | |
| 11 | 44 | 4 | 3 | 47 | 10 | 4 | >2 | — | 2 | | 64 | 6 | 87 | 6 |
| 12 | 60 | 1 | 2 | 54 | 13 | 4 | 0.46 | 0.2 | 2 | <10 | 11 | 3 | 55 | 4 |

-continued

| | | | | | | | MDA: Inhib. of invasion: 0.5 × eff. of 10 μM Y-27632 at (μM) | | | | % hERG inhibition in transfected HEK (n = 3) | | | |
|---|---|---|---|---|---|---|---|---|---|---|---|---|---|---|---|
| | MDA tox: 50% tox. at (μM) | | | PBMC tox.: 50% tox. at (μM) | | | (+ MDA tox. under these cond.) | | | | at 1 μM | | at 10 μM | |
| N° | av | SD | n | av | SD | n | av | SD | n | % tox | av | SEM | av | SEM |
| 13 | 93 | 5 | 3 | 34 | 18 | 6 | >5 | — | 2 | | | | | |
| 14 | 70 | 8 | 3 | 20 | 8 | 4 | >2.5 | — | 2 | | | | | |
| 15 | >>44 | — | 2 | 36 | 18 | 4 | 5.00 | 0.0 | 2 | <10 | | | | |
| 16 | 78 | 6 | 4 | 10 | 4 | 5 | ≥4.6 | — | 2 | | | | | |
| 17 | >100 | — | 2 | >100 | — | 4 | 3.00 | 1.2 | 2 | <10 | | | | |
| 18 | >100 | — | 2 | >100 | — | 4 | 3.45 | 1.6 | 2 | <10 | | | | |
| 19 | >100 | — | 2 | >100 | — | 4 | >5 | — | 2 | | | | | |
| 20 | >100 | — | 2 | >100 | — | 4 | 0.85 | 0.2 | 2 | <10 | | | | |
| 21 | >100 | — | 2 | >100 | — | 4 | 2.05 | 0.7 | 2 | <10 | | | | |
| 22 | >100 | — | 2 | >100 | — | 4 | 2.25 | 0.0 | 2 | <10 | | | | |
| 23 | >100 | — | 2 | >70 | — | 4 | >5 | — | 2 | | | | | |
| 24 | >100 | — | 2 | ≥100 | — | 4 | 3.55 | 1.1 | 2 | <10 | | | | |
| 25 | 46 | 13 | 2 | 88 | 10 | 4 | <0.5 | — | 2 | <10 | | | | |
| 26 | 73 | 7 | 2 | 85 | 11 | 4 | 3.60 | 0.5 | 2 | <10 | | | | |
| 27 | 66 | 6 | 2 | 61 | 5 | 4 | 2.80 | 0.6 | 2 | <10 | | | | |
| 28 | 35 | 10 | 2 | 49 | 2 | 4 | 0.26 | 0.1 | 2 | <10 | | | | |
| 29 | 33 | 8 | 2 | 44 | 6 | 4 | 0.15 | 0.0 | 2 | <10 | | | | |
| 30 | 75 | 25 | 2 | >100 | — | 4 | 0.28 | 0.1 | 2 | <10 | | | | |
| 31 | 95 | 5 | 2 | 92 | 12 | 4 | 0.10 | — | 1 | <10 | | | | |
| 32 | >>100 | — | 2 | >>100 | | 2 | 13.30 | 0.3 | 2 | <10 | | | | |
| 33 | 118 | 3 | 2 | 130 | 10 | 4 | 2.13 | 0.9 | 2 | <10 | | | | |
| 34 | 98 | 13 | 2 | >100 | — | 4 | 0.40 | — | 1 | <10 | | | | |
| 35 | 59 | 2 | 4 | 128 | 8 | 4 | 0.55 | 0.4 | 5 | <10 | 4 | 3 | 30 | 4 |
| 36 | >>100 | — | 3 | 58 | 38 | 6 | >5 | — | 2 | | | | | |
| 37 | >>100 | — | 2 | >>100 | — | 4 | 3.75 | 1.3 | 2 | <10 | | | | |
| 38 | >>100 | — | 2 | >>100 | — | 4 | 3.75 | 1.3 | 2 | <10 | | | | |
| 39 | 19 | 2 | 2 | 74 | 16 | 4 | 1.45 | 0.2 | 2 | <10 | | | | |
| 40 | 73 | 9 | 4 | >100 | — | 6 | 0.75 | 0.3 | 2 | <10 | 26 | 5 | 59 | 8 |
| 41 | ≥80 | — | 2 | >100 | — | 4 | 1.50 | 1.0 | 2 | <10 | 8 | 2 | 53 | 1 |
| 42 | ≥100 | — | 2 | >100 | — | 4 | 0.20 | — | 1 | <10 | | | | |
| 43 | >100 | — | 2 | >100 | — | 4 | 3.25 | 0.8 | 2 | <10 | | | | |
| 44 | >100 | — | 2 | >100 | — | 4 | 1.15 | 0.3 | 2 | <10 | | | | |
| 45 | >100 | — | 2 | >100 | — | 4 | 0.38 | 0.1 | 2 | <10 | | | | |
| 46 | >100 | — | 2 | >100 | — | 4 | 7.50 | 2.5 | 2 | | | | | |
| 47 | >100 | — | 2 | >100 | — | 4 | 2.20 | 0.1 | 2 | <10 | | | | |
| 48 | 80 | 20 | 2 | 26 | 2 | 4 | 0.75 | 0.3 | 2 | <10 | | | | |
| 49 | ≥100 | — | 2 | >100 | — | 4 | 0.88 | 0.1 | 2 | <10 | | | | |
| 50 | ≥100 | — | 2 | >100 | — | 4 | 1.88 | 0.6 | 2 | <10 | | | | |
| 51 | ≥100 | — | 2 | >100 | — | 4 | 0.30 | — | 1 | <10 | | | | | av. Means average
SD means standard deviation
n is the number of samples
SEM means Standard Error of Mean Example 16: Comparative Data Three compounds of the present invention (compounds 1, 3 and 4) are compared (MDA toxicity, PBMC toxicity, invasiveness inhibition and hERG inhibition) to respectively three compounds which are already specifically or generically disclosed in WO2009087238.

More precisely:
compound 1 according to the invention is compared to compound numbered C88 in WO2009087238 (on page 66):

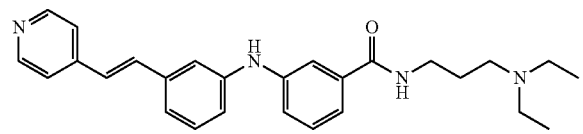 [SMILES: CCN(CC)CCCNC(=O)c1cccc(Nc2cccc(/C=C/c3ccncc3)c2)c1]

(compound C88 in WO2009087238, hereinafter numbered 112)

compound 3 according to the invention is compared to a compound hereinafter numbered 583 which corresponds to the following formula:

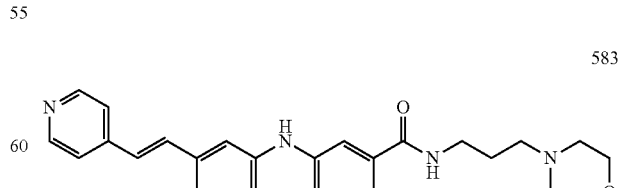

583 compound 4 according to the invention is compared to a compound hereinafter numbered 585 which corresponds to the following formula:

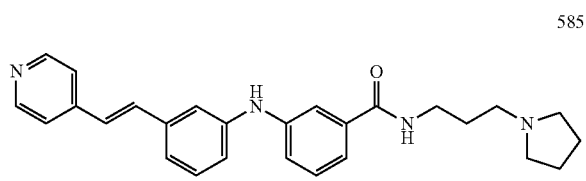 [SMILES: O=C(NCCCN1CCCC1)c1cccc(Nc2cccc(/C=C/c3ccncc3)c2)c1]

585

The table below indicates the toxicity on MDA-MB231, on PBMC, the anti-invasive effect, and the inhibition of hERG channel.

using the procedure 1. Compound C88 is considered to having anti-invasive properties.

Secondly compound C88 was compared to compound 1 of the present invention using the procedure 2.

| N° | MDA tox: 50% tox. at (μM) | | | PBMC tox.: 50% tox. at (μM) | | | MDA: Inhib. of invasion: 0.5 × eff. of 10 μM Y-27632 at (μM) | | | (+ MDA tox. under these cond.) | % hERG inhibition in transfected HEK (n = 3) | | | |
|---|---|---|---|---|---|---|---|---|---|---|---|---|---|---|
| | | | | | | | | | | | at 1 μM | | at 10 μM | |
| | av. | SD | n | av. | SD | n | av. | SD | n | % tox. | av. | SEM | av. | SEM |
| 112 (C88) (comparative) | 10 | 0 | 4 | 10 | 2 | 8 | 0.39 | 0.13 | 7 | <10 | 55 | 11 | 92 | 3 |
| 1 (invention) | 46 | 10 | 5 | 51 | 11 | 10 | 0.13 | 0.09 | 9 | <10 | 13 | 2 | 47 | 2 |
| 583 (comparative) | 21 | 1 | 2 | 18 | 3 | 8 | 0.25 | 0.05 | 2 | <10 | 36 | 7 | 74 | 6 |
| 3 (invention) | 51 | 0 | 2 | 51 | 10 | 4 | 0.29 | 0.14 | 4 | <10 | 14 | 4 | 54 | 4 |
| 585 (comparative) | 10 | — | 1 | 9 | 1 | 6 | 0.30 | 0.05 | 2 | <10 | 42 | 7 | 77 | 9 |
| 4 (invention) | 54 | 2 | 2 | 42 | 11 | 4 | 0.21 | 0.11 | 4 | <10 | 6 | 0 | 59 | 2 | av. Means average
SD means standard deviation
n is the number of samples
SEM means Standard Error of Mean This table shows that the claimed compounds (I) possess improved properties compared to previously known compounds.

More particularly, compound 1 according to the present invention is less toxic on MDA-MB231 and on PBMC, more potent in invasiveness inhibition, and displays less hERG inhibition than compound C88 (112).

More particularly, compound 3 according to the present invention is less toxic on MDA-MB231 and on PBMC, and displays less hERG inhibition than compound 583.

More particularly, compound 4 according to the present invention is less toxic on MDA-MB231 and on PBMC, more potent in invasiveness inhibition, and displays less hERG inhibition than compound 585.

Example 17: Comparative Data 2 sets of experiments were performed on one comparative compound as specifically disclosed in WO2009/087238 and one claimed compound using a reference compound "C88" as disclosed in WO2009/087238 and as mentioned in example 16.

Said compound C88 was used as reference to compare efficiency of invasiveness inhibition between two series of compounds.

First compound C88 was compared to FMMB46.1 as disclosed in WO2009/087238 (on page 95) of formula It is to be noted that both Procedures 1 and 2 are invasion assays to test effect of drug compounds on invasion. They are both fully identical except for the time of incubation with the drug.

In the first set of experiments, anti-invasive activity was detected when cells are treated with compound C88, but no effect was observed with FMMB46.1 (Table 1).

In the second set of experiments, anti-invasive activity is detected when cells are treated with compounds C88 and compound 1.

First Set of Experiments—Results:

TABLE 1

| | Invasion av. | SD | n |
|---|---|---|---|
| C88 | 1 | 0 | 4 |
| FMMB46.1 of WO2009/087238 | 0.02 | 0.19 | 4 | av. Means average
SD means standard deviation
n is the number of samples

Here, invasion (into collagen) is the number of cells per valid field at 50 μm fold inhibitory effect compared to 10 μM Y-27632.

Standard Operating Procedure 1:

Said procedure is as described in example 15 except with respect to (i) the last step during day 1 "preparation of the invasion assay" and "treatment with the drugs" and days 2 and 3 which are detailed hereinafter and (ii) the fact that no concentration nor toxicity is determined at the end.

The different steps are as follows:

Preparation of the Invasion Assay (on Ice; Start During the Centrifugation of the Cells):

mix on ice in a pre-chilled tube: example for a 3.4 mg/ml collagen stock solution; volumes of collagen and water to be adapted according to the stock concentration of each collagen lot:

2.8 ml 2.5×MEM

441 µl water

140 µl 1 M Hepes

49 µl 1 N NaOH 3.5 ml 3.4 mg/ml collagen stock solution (yielding 1.7 mg/ml collagen in 7 ml)

homogenize by pipetting gently up and down (keep on ice)

add 70 µl of the 10×10⁶ cells/ml cell suspension, homogenize by pipetting gently up and down (yields 0.1×10⁶ cells/ml in 1.7 mg/ml collagen in 7 ml 1×MEM+20 µM Hepes) (keep on ice)

distribute 100 µl/well (i. e. 10000 cells/well) into the coated wells of the plate for the invasion assay (all on ice)

centrifuge 5' with 200×g at 4° C. (e. g. 1000 rpm in a Jouan GR412 centrifuge)

add 200 µl/well PBS to all free wells incubate 30' at 37° C./5% CO$_2$ (solidification of the collagen)

Treatment with the Drugs:

add each 33 µl/well of the 4× concentrated drug solutions in MEM+0.1% FBS to the corresponding wells in all three plates, according to the plate maps above incubate 24 h at 37° C./5% CO$_2$ Day 2: Addition of FBS to Stimulate the Invasion:

Microscopic Observation after 24 h of Treatment:

examine the cells of the viability assays

Addition of FBS (Under a Cell Culture Hood):

prepare MEM+5% FBS: 7.2 ml MEM without serum+0.8 ml FBS (freshly thawed aliquot or rest of the aliquot thawed the day before if kept at 4° C.)

add 33 µl/well to all wells of invasion and viability assays incubate 24 h at 37° C./5% CO$_2$ Day 3: Stop:

Microscopic Observation after 48 h of Treatment:

examine the cells of the viability assays

Invasion Assays: Fixation and Staining (Formaldehyde Must be Manipulated Under a Fume Cupboard):

freshly prepare 1 µg/ml Hoechst 33342 in 18.5% formaldehyde: 5 ml PBS (not necessarily sterile)+5 ml 37% formaldehyde+1 µl 10 mg/ml Hoechst 33342 (note: for one plate, a smaller volume would be sufficient, but the minimal pipetted volume should not be below 1 µl)

add 50 µl/well to all wells of the invasion assay (yields 4.3% formaldehyde final)

seal with black film (provided with the plates)

incubate at least 7 h at RT.

The analysis as performed in day 5 in example 15 is performed exactly under the same conditions in day 3 in the framework of the present procedure 1.

Second Set of Experiments—Results:

TABLE 2

| | Invasion Av. | SD | n |
|---|---|---|---|
| C88 | 0.39 | 0.13 | 4 |
| Compound 1 | 0.13 | 0.09 | 4 | av. Means average
SD means standard deviation
n is the number of samples

Here, invasion (into collagen) is the concentration of the compound necessary to reach 50% of the inhibition effect compared to 10 µM Y-27632.

Standard operating procedure 2 is exactly the same as the procedure as described in example 15.

CONCLUSION

As far as compound 1 shows better invasion results than compound C88, which itself shows better invasion results than compound FMMB46.1, it is concluded that unexpected properties have been discovered by the inventors, without any guidance in the teaching of WO2009/087238.

The compounds according to the present invention demonstrate an anti-invasive effect predictive for their activity against cancer.

Therefore, the result of the tests carried out on the compounds disclosed in the present invention show that said compounds may be useful for inhibiting and/or preventing and/or treating cancer. The following type of cancer may more particularly be treated by the compounds according to the present invention: colorectal cancer, pancreatic cancer, lung cancer including non-small cell lung cancer, breast cancer, bladder cancer, gall bladder cancer, thyroid cancer, melanoma, liver cancer, uterine/cervical cancer, oesophageal cancer, kidney cancer, ovarian cancer, prostate cancer, head and neck cancer, and stomach cancer, etc.

For this purpose an effective amount of a said compound may be administered to a patient suffering from cancer.

The present invention is also related to the use of at least a compound chosen among a compound of any one of formula (I), (I'), (Ia), (Ib), (Ic), (Id) and (Ie) as defined above, and compounds (1) to (51) as defined above, or one of its pharmaceutically acceptable salts according to the present invention for the manufacture of a pharmaceutical composition intended for the treatment of cancer.

The present invention also encompasses pharmaceutical compositions comprising at least a compound chosen among compounds of formulae (I), (I'), (Ia), (Ib), (Ic), (Id) and (Ie) as defined above and compounds (1) to (51) as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present invention is also related to the use of a compound of any one of formulae (I), (I'), (Ia), (Ib), (Ic), (Id) and (Ie) as defined above, and compounds (1) to (51) as defined above, or one of its pharmaceutically acceptable salts according to the present invention for the manufacture of a pharmaceutical composition intended for inhibiting and/or preventing and/or treating cancer.

The present invention further relates to a method of treatment of patients suffering form cancer, which comprises at least a step of administration to a patient suffering thereof of an effective amount of a compound of any one of formulae (I), (I'), (Ia), (Ib), (Ic), (Id), and (Ie) as defined above and (1) to (51) or one of its pharmaceutically acceptable salts.

The invention claimed is:

1. A compound of formula (I):

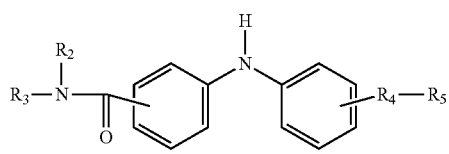

(I)

wherein
$R_2$ is a hydrogen atom or a $(C_1$-$C_4)$alkyl group;
$R_3$ is a 2-pyridyl group, 3-pyridyl group or a 4-pyridyl group;
$R_4$ is a carbonyl group or a sulfonyl group; and
$R_5$ is a —NH—$(CH_2)_a$—$NR_6R_7$ group, with a being an integer from 1 to 4, $R_6$ and $R_7$ representing independently a $(C_1$-$C_4)$alkyl group;
or any one of its pharmaceutically acceptable salt.

2. A compound of formula (I) according to claim 1 wherein
$R_2$ is a hydrogen atom or a methyl group;
$R_3$ is a 2-pyridyl or a 4-pyridyl group;
$R_4$ is a carbonyl group or a sulfonyl group; and
$R_5$ is a —NH—$(CH_2)_a$—$NR_6R_7$ group, with a being an integer from 2 to 3, $R_6$ and $R_7$ representing an ethyl group;
or any one of its pharmaceutically acceptable salt.

3. Compound of formula (I) according to claim 1 wherein the group —NH— between the two phenylene groups and the group —$R_4$-$R_5$ are in position meta from each other.

4. A compound of formula (I) according to claim 1, wherein $R_4$ is a carbonyl group and
$R_2$ is a hydrogen atom or a $(C_1$-$C_4)$alkyl group;
$R_3$ is a 2-pyridyl group, 3-pyridyl group or a 4-pyridyl group; and
$R_5$ is a —NH—$(CH_2)_a$—$NR_6R_7$ group, with a being an integer from 1 to 4, $R_6$ and $R_7$ representing independently a $(C_1$-$C_4)$alkyl group;
or any one of its pharmaceutically acceptable salt.

5. A compound of formula (I) according to claim 1 chosen among
(1) N-(3-(diethylamino)propyl)-3-((3-(pyridin-4-ylcarbamoyl)phenyl)amino) benzamide
(2) 3-((4-((3-(diethylamino)propyl)carbamoyl)phenyl)amino)-N-(pyridin-4-yl)benzamide
(5) 3-((3-(N-(3-(diethylamino)propyl)sulfamoyl)phenyl)amino)-N-(pyridin-4-yl)benzamide
(11) N-(3-(diethylamino)propyl)-3-((3-(pyridin-2-ylcarbamoyl)phenyl)amino) benzamide
(13) N-(3-(diethylamino)propyl)-3-((4-(pyridin-4-ylcarbamoyl)phenyl)amino) benzamide
(17) 3-((3-((3-(diethylamino)propyl)carbamoyl)phenyl)amino)-N-methyl-N-(pyridin-4-yl)benzamide
(19) 3-((3-(N-(3-(diethylamino)propyl)sulfamoyl)phenyl)amino)-N-methyl-N-(pyridin-4-yl)benzamide
and their pharmaceutically acceptable salts.

6. Process for the preparation of compounds of formula (I) according to claim 1 comprising reacting a compound of formula (II)

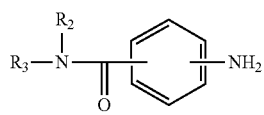

(II)

wherein $R_2$ and $R_3$ are as defined in claim 1,
with a compound of formula (III)

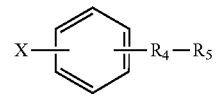

(III)

wherein X is a chlorine atom, an iodine atom or a bromine atom, and $R_4$ and $R_5$ are as defined in claim 1, wherein the reaction takes place in a protic solvent, in presence of an inorganic base, in the presence of a diphosphine and of an organometallic catalyst, the temperature being increased from 80 to 120° C. under an inert gas.

7. A method of treating a patient, the method comprising administering to a patient a medicine comprising an effective amount of compound of formula (I) according to claim 1 to treat breast cancer and kidney cancer.

8. Pharmaceutical composition comprising at least one compound of formula (I) as defined in claim 1 and a pharmaceutically acceptable excipient.

* * * * *